(12) United States Patent
Rosen et al.

(10) Patent No.: US 12,740,855 B2
(45) Date of Patent: Sep. 22, 2026

(54) INTRAOCULAR LENSES FOR PRESBYOPIA TREATMENT

(71) Applicant: AMO Groningen B.V., Groningen (NL)

(72) Inventors: Robert Rosen, Groningen (NL); Hendrik A. Weeber, Groningen (NL)

(73) Assignee: AMO Groningen B.V., Groningen (NL)

( * ) Notice: Subject to any disclaimer, the term of this patent is extended or adjusted under 35 U.S.C. 154(b) by 813 days.

(21) Appl. No.: 18/063,672

(22) Filed: Dec. 8, 2022

(65) Prior Publication Data

US 2023/0105462 A1 Apr. 6, 2023

Related U.S. Application Data

(62) Division of application No. 16/015,119, filed on Jun. 21, 2018, now Pat. No. 11,523,897.

(Continued)

(51) Int. Cl.

*A61F 2/16* (2006.01)
*G02C 7/04* (2006.01)
*A61F 2/14* (2006.01)

(52) U.S. Cl.

CPC .......... *A61F 2/1627* (2013.01); *A61F 2/1618* (2013.01); *A61F 2/164* (2015.04);

(Continued)

(58) Field of Classification Search

CPC .................................................... A61F 2/1654

See application file for complete search history.

(56) References Cited

U.S. PATENT DOCUMENTS 3,367,734 A 2/1968 Karl et al.
3,722,986 A 3/1973 Tagnon (Continued)

FOREIGN PATENT DOCUMENTS

AU 2005230194 B2 12/2010
CA 2501217 A1 4/2004

(Continued)

OTHER PUBLICATIONS

Albert D.M., "(Book Review) Intraocular Lenses: Evolution, Designs, Complications, and Pathology, by David Apple et al.," Archieves of Opthalmology, 1990, vol. 108, pp. 650.

(Continued)

*Primary Examiner* — Javier G Blanco

(57) ABSTRACT

Apparatuses, systems and methods for providing improved ophthalmic lenses, particularly intraocular lenses (IOLs), include features for reducing dysphotopsia effects, such as haloes and glare. Exemplary ophthalmic lenses may include a central zone with a first set of two echelettes arranged around the optical axis, the first set having a profile in r-squared space. A middle zone includes a second set of two echelettes arranged around the optical axis, the second set having a profile in r-squared space that is different than the profile of the first set. A peripheral zone includes a third set of two echelettes arranged around the optical axis, the third set having a profile in r-squared space that is different than the profile of the first set and the profile of the second set, the third set being repeated in series on the peripheral zone.

2 Claims, 9 Drawing Sheets

Related U.S. Application Data

(60) Provisional application No. 62/524,128, filed on Jun. 23, 2017.

(52) U.S. Cl.
CPC .......... *A61F 2/1648* (2013.01); *A61F 2/1654* (2013.01); *G02C 7/04* (2013.01); *A61F 2/145* (2013.01); *A61F 2/1602* (2013.01); *A61F 2240/001* (2013.01); *G02C 7/041* (2013.01); *G02C 2202/20* (2013.01)

(56) References Cited

U.S. PATENT DOCUMENTS 4,210,391 A 7/1980 Cohen et al.
4,338,005 A 7/1982 Cohen
4,340,283 A 7/1982 Cohen
4,460,275 A 7/1984 Spriggs
4,504,892 A 3/1985 Zulfilar
4,504,982 A 3/1985 Burk
4,580,883 A 4/1986 Shinohara
4,606,626 A 8/1986 Shinohara
4,637,697 A 1/1987 Freeman
4,640,593 A 2/1987 Shinohara
4,641,934 A 2/1987 Freeman
4,642,112 A 2/1987 Freeman
4,655,565 A 4/1987 Freeman
4,710,193 A 12/1987 Volk
4,762,408 A 8/1988 Shinohara
4,778,462 A 10/1988 Grendahl
4,795,462 A 1/1989 Grendahl
4,798,608 A 1/1989 Grendahl
4,798,609 A 1/1989 Grendahl
4,856,234 A 8/1989 Goins
4,856,889 A 8/1989 Guilino et al.
4,881,804 A 11/1989 Cohen
4,881,805 A 11/1989 Cohen
4,898,461 A 2/1990 Portney
4,932,970 A 6/1990 Portney
4,936,666 A 6/1990 Futhey
4,957,506 A 9/1990 Mercier
4,978,211 A 12/1990 Cornu et al.
4,995,714 A 2/1991 Cohen
4,995,715 A 2/1991 Cohen
5,016,977 A 5/1991 Baude et al.
5,017,000 A 5/1991 Cohen
5,019,098 A 5/1991 Mercier
5,045,905 A 9/1991 Motai et al.
5,050,981 A 9/1991 Roffman
5,054,905 A 10/1991 Cohen
5,056,908 A 10/1991 Cohen
5,061,058 A 10/1991 Guilino et al.
5,066,301 A 11/1991 Wiley
5,076,684 A 12/1991 Simpson et al.
5,089,023 A 2/1992 Swanson
5,089,024 A 2/1992 Christie et al.
5,096,285 A 3/1992 Silberman
5,100,226 A 3/1992 Freeman
5,104,212 A 4/1992 Taboury et al.
5,112,351 A 5/1992 Christie et al.
5,114,220 A 5/1992 Baude et al.
5,116,111 A 5/1992 Simpson et al.
5,117,306 A 5/1992 Cohen
5,120,120 A 6/1992 Cohen
5,121,979 A 6/1992 Cohen
5,121,980 A 6/1992 Cohen
5,129,718 A 7/1992 Futhey et al.
5,144,483 A 9/1992 Cohen
5,148,205 A 9/1992 Guilino et al.
5,161,057 A 11/1992 Johnson
5,173,723 A 12/1992 Volk et al.
5,178,636 A 1/1993 Silberman
5,191,366 A 3/1993 Kashiwagi
5,220,359 A 6/1993 Roffman
5,225,858 A 7/1993 Portney
5,229,797 A 7/1993 Futhey et al.
5,236,970 A 8/1993 Christ et al.
5,257,132 A 10/1993 Ceglio et al.
5,260,727 A 11/1993 Oksman et al.
5,322,649 A 6/1994 Rheinish et al.
5,344,447 A 9/1994 Swanson
5,349,394 A 9/1994 Freeman et al.
5,349,471 A 9/1994 Morris et al.
5,381,190 A 1/1995 Rehse et al.
5,384,606 A 1/1995 Koch et al.
5,408,281 A 4/1995 Zhang
5,443,506 A 8/1995 Garabet
5,443,507 A 8/1995 Jacobi
5,444,106 A 8/1995 Zhou et al.
5,446,508 A 8/1995 Kitchen
5,448,312 A 9/1995 Roffman et al.
5,485,228 A 1/1996 Roffman et al.
5,581,405 A 12/1996 Meyers et al.
5,589,982 A 12/1996 Faklis et al.
5,629,800 A 5/1997 Hamblen
5,652,638 A 7/1997 Roffman et al.
5,674,284 A 10/1997 Chang et al.
5,682,223 A 10/1997 Menezes et al.
5,683,457 A 11/1997 Gupta et al.
5,684,560 A 11/1997 Roffman et al.
5,684,595 A 11/1997 Kato et al.
5,699,142 A 12/1997 Lee et al.
5,715,031 A 2/1998 Roffman et al.
5,715,091 A 2/1998 Meyers
5,724,258 A 3/1998 Roffman
5,728,156 A 3/1998 Gupta et al.
5,748,282 A 5/1998 Freeman
5,760,871 A 6/1998 Kosoburd et al.
5,777,719 A 7/1998 Williams et al.
5,796,462 A 8/1998 Roffman et al.
5,800,532 A 9/1998 Lieberman
5,805,260 A 9/1998 Roffman et al.
5,822,091 A 10/1998 Baker
5,838,496 A 11/1998 Maruyama et al.
5,847,802 A 12/1998 Menezes et al.
5,888,122 A 3/1999 Gupta et al.
5,895,422 A 4/1999 Hauber
5,895,610 A 4/1999 Chang et al.
5,929,969 A 7/1999 Roffman
5,968,094 A 10/1999 Werblin et al.
5,968,095 A 10/1999 Norrby
5,982,543 A 11/1999 Fiala
6,007,747 A 12/1999 Blake et al.
6,019,472 A 2/2000 Koester et al.
6,050,687 A 4/2000 Bille et al.
6,070,980 A 6/2000 Obara et al.
6,082,856 A 7/2000 Dunn et al.
6,086,204 A 7/2000 Magnante
6,089,711 A 7/2000 Blankenbecler et al.
6,095,651 A 8/2000 Williams et al.
6,120,148 A 9/2000 Fiala et al.
6,126,283 A 10/2000 Wen et al.
6,126,286 A 10/2000 Portney
6,139,145 A 10/2000 Israel
6,142,625 A 11/2000 Sawano et al.
6,145,987 A 11/2000 Baude et al.
6,154,323 A 11/2000 Kamo
6,199,986 B1 3/2001 Williams et al.
6,210,005 B1 4/2001 Portney
6,215,096 B1 4/2001 Von Wallfeld et al.
6,224,211 B1 5/2001 Gordon
6,231,603 B1 5/2001 Lang et al.
6,270,220 B1 8/2001 Keren
6,271,915 B1 8/2001 Frey et al.
6,325,510 B1 12/2001 Golub et al.
6,338,559 B1 1/2002 Williams et al.
6,353,503 B1 3/2002 Spitzer et al.
6,413,276 B1 7/2002 Werblin
6,429,972 B1 8/2002 Ota et al.
6,439,720 B1 8/2002 Graves et al.
6,457,826 B1 10/2002 Lett
6,462,874 B1 10/2002 Soskind
6,464,355 B1 10/2002 Gil
6,474,814 B1 11/2002 Griffin

(56) References Cited

U.S. PATENT DOCUMENTS 6,488,708 B2 12/2002 Sarfarazi
6,491,721 B2 12/2002 Freeman et al.
6,497,483 B2 12/2002 Frey et al.
6,511,180 B2 1/2003 Guirao et al.
6,520,638 B1 2/2003 Roffman et al.
6,527,389 B2 3/2003 Portney
6,533,416 B1 3/2003 Fermigier et al.
6,536,899 B1 3/2003 Fiala
6,537,317 B1 3/2003 Steinert et al.
6,547,391 B2 4/2003 Ross, III et al.
6,547,822 B1 4/2003 Lang
6,554,425 B1 4/2003 Roffman et al.
6,554,859 B1 4/2003 Lang et al.
6,557,992 B1 5/2003 Dwyer et al.
6,576,012 B2 6/2003 Lang
6,582,076 B1 6/2003 Roffman et al.
6,585,375 B2 7/2003 Donitzky et al.
6,609,673 B1 8/2003 Johnson
6,609,793 B2 8/2003 Norrby et al.
6,616,275 B1 9/2003 Dick et al.
6,655,802 B2 12/2003 Zimmermann et al.
6,685,315 B1 2/2004 De
6,705,729 B2 3/2004 Piers et al.
6,709,103 B1 3/2004 Roffman et al.
6,755,524 B2 6/2004 Rubinstein et al.
6,791,754 B2 9/2004 Ogawa
6,802,605 B2 10/2004 Cox et al.
6,808,262 B2 10/2004 Chapoy et al.
6,818,158 B2 11/2004 Pham et al.
6,827,444 B2 12/2004 Williams et al.
6,830,332 B2 12/2004 Piers et al.
6,835,204 B1 12/2004 Stork et al.
6,846,326 B2 1/2005 Zadno-Azizi et al.
6,848,790 B1 2/2005 Dick et al.
6,851,803 B2 2/2005 Wooley et al.
6,884,261 B2 4/2005 Zadno-Azizi et al.
6,923,539 B2 8/2005 Simpson et al.
6,923,540 B2 8/2005 Ye et al.
6,951,391 B2 10/2005 Morris et al.
6,957,891 B2 10/2005 Fiala
6,972,032 B2 12/2005 Aharoni et al.
6,986,578 B2 1/2006 Jones
7,025,456 B2 4/2006 Morris et al.
7,036,931 B2 5/2006 Lindacher et al.
7,048,759 B2 5/2006 Bogaert et al.
7,048,760 B2 5/2006 Cumming
7,061,693 B2 6/2006 Zalevsky
7,073,906 B1 7/2006 Portney
7,093,938 B2 8/2006 Morris et al.
7,111,938 B2 9/2006 Andino et al.
7,137,702 B2 11/2006 Piers et al.
7,156,516 B2 1/2007 Morris et al.
7,159,983 B2 1/2007 Menezes et al.
7,188,949 B2 3/2007 Bandhauer et al.
7,198,640 B2 4/2007 Nguyen
7,217,375 B2 5/2007 Lai
7,221,513 B2 5/2007 Cho et al.
7,232,218 B2 6/2007 Morris et al.
7,287,852 B2 10/2007 Fiala
7,293,873 B2 11/2007 Dai et al.
7,365,917 B2 4/2008 Zalevsky
7,377,640 B2 5/2008 Piers et al.
7,377,641 B2 5/2008 Piers et al.
7,441,894 B2 10/2008 Zhang et al.
7,455,404 B2 11/2008 Bandhauer et al.
7,475,986 B2 1/2009 Dai et al.
7,481,532 B2 1/2009 Hong et al.
7,543,937 B2 6/2009 Piers et al.
7,572,007 B2 8/2009 Simpson
7,604,350 B2 10/2009 Dursteler et al.
7,615,073 B2 11/2009 Deacon et al.
7,654,667 B2 2/2010 Blum et al.
7,670,371 B2 3/2010 Piers et al.
7,677,725 B2 3/2010 Piers et al.
7,717,558 B2 5/2010 Hong et al.
7,753,521 B2 7/2010 Wooley et al.
7,871,162 B2 1/2011 Weeber
7,883,207 B2 2/2011 Iyer et al.
7,896,916 B2 3/2011 Piers et al.
7,922,326 B2 4/2011 Bandhauer et al.
7,984,990 B2 7/2011 Bandhauer et al.
7,998,198 B2 8/2011 Angelopoulos et al.
8,128,222 B2 3/2012 Portney
8,157,374 B2 4/2012 Bandhauer et al.
8,192,022 B2 6/2012 Zalevsky
8,197,063 B2 6/2012 Iyer et al.
8,216,307 B2 7/2012 Schaper, Jr.
8,231,219 B2 7/2012 Weeber
8,231,673 B2 7/2012 Sacharoff et al.
8,235,525 B2 8/2012 Lesage et al.
8,240,850 B2 8/2012 Apter et al.
8,241,354 B2 8/2012 Hong et al.
8,262,728 B2 9/2012 Zhang et al.
8,292,953 B2 10/2012 Weeber et al.
8,382,281 B2 2/2013 Weeber
8,388,137 B2 3/2013 Dreher et al.
8,430,508 B2 4/2013 Weeber
8,444,267 B2 5/2013 Weeber et al.
8,480,228 B2 7/2013 Weeber
8,500,805 B2 8/2013 Kobayashi et al.
8,506,075 B2 8/2013 Bandhauer et al.
8,529,623 B2 9/2013 Piers et al.
8,556,416 B2 10/2013 Lawu
8,556,417 B2 10/2013 Das et al.
8,573,775 B2 11/2013 Weeber
8,619,362 B2 12/2013 Portney
8,636,796 B2 1/2014 Houbrechts et al.
8,652,205 B2 2/2014 Hong et al.
8,678,583 B2 3/2014 Cohen
8,709,079 B2 4/2014 Zhang et al.
8,734,511 B2 5/2014 Weeber et al.
8,740,978 B2 6/2014 Weeber et al.
8,747,466 B2 6/2014 Weeber et al.
8,755,117 B2 6/2014 Kobayashi et al.
8,771,348 B2 7/2014 Zhao
8,827,446 B2 9/2014 Iyer et al.
8,906,089 B2 12/2014 Piers et al.
9,069,185 B2 6/2015 Zhao
9,078,745 B2 7/2015 Zhang et al.
9,122,074 B2 9/2015 Piers et al.
9,164,201 B2 10/2015 Fermigier et al.
9,223,148 B2 12/2015 Fiala et al.
9,304,329 B2 4/2016 Zhao
9,310,624 B2 4/2016 Argal et al.
9,320,594 B2 4/2016 Schwiegerling
9,329,309 B2 5/2016 Van
9,335,563 B2 5/2016 Weeber
9,335,564 B2 5/2016 Choi et al.
9,355,563 B2 5/2016 Altintas et al.
9,370,416 B2 6/2016 Argal et al.
9,518,864 B2 12/2016 Grossinger et al.
9,563,070 B2 2/2017 Ando et al.
9,622,856 B2 4/2017 Weeber et al.
9,869,580 B2 1/2018 Grossinger et al.
9,925,041 B2 3/2018 Gerlach et al.
9,931,200 B2 4/2018 Van et al.
10,698,234 B2 6/2020 Zhao
11,022,815 B2 6/2021 Weeber
11,156,853 B2 10/2021 Weeber et al.
11,262,598 B2 3/2022 Weeber et al.
11,327,210 B2 5/2022 Weeber et al.
11,497,599 B2 11/2022 Cánovas Vidal et al.
11,573,433 B2 2/2023 Weeber et al.
2001/0018612 A1 8/2001 Carson et al.
2002/0082690 A1 6/2002 Sarbadhikari
2002/0093701 A1 7/2002 Zhang et al.
2002/0105617 A1 8/2002 Norrby et al.
2002/0118337 A1 8/2002 Perrott et al.
2002/0119965 A1 8/2002 Piccolo et al.
2002/0122153 A1 9/2002 Piers et al.
2003/0014107 A1 1/2003 Reynard
2003/0063254 A1 4/2003 Piers et al.
2003/0076478 A1 4/2003 Cox
2003/0169491 A1 9/2003 Bender et al.

(56) References Cited

U.S. PATENT DOCUMENTS

2003/0171808 A1 9/2003 Phillips
2004/0021824 A1 2/2004 Ye et al.
2004/0080710 A1 4/2004 Wooley et al.
2004/0085515 A1 5/2004 Roffman et al.
2004/0088050 A1 5/2004 Norrby et al.
2004/0106992 A1 6/2004 Lang et al.
2004/0111153 A1 6/2004 Woods et al.
2004/0138746 A1 7/2004 Aharoni et al.
2004/0150789 A1 8/2004 Jones
2004/0156014 A1 8/2004 Piers et al.
2004/0169820 A1 9/2004 Dai et al.
2004/0189981 A1 9/2004 Ross et al.
2004/0230299 A1 11/2004 Simpson et al.
2004/0246440 A1 12/2004 Andino et al.
2004/0252274 A1 12/2004 Morris et al.
2005/0057720 A1 3/2005 Morris et al.
2005/0096226 A1 5/2005 Stock et al.
2005/0099589 A1 5/2005 Ishak
2005/0128432 A1 6/2005 Altmann
2005/0203619 A1 9/2005 Altmann
2005/0259222 A1 11/2005 Kelch et al.
2005/0264757 A1 12/2005 Morris et al.
2005/0267575 A1 12/2005 Nguyen et al.
2006/0004446 A1 1/2006 Aharoni et al.
2006/0009816 A1 1/2006 Fang et al.
2006/0030938 A1 2/2006 Altmann
2006/0034003 A1 2/2006 Zalevsky
2006/0055883 A1 3/2006 Morris et al.
2006/0066808 A1 3/2006 Blum et al.
2006/0098162 A1 5/2006 Bandhauer et al.
2006/0098163 A1 5/2006 Bandhauer et al.
2006/0109421 A1 5/2006 Ye et al.
2006/0116763 A1 6/2006 Simpson
2006/0116764 A1 6/2006 Simpson
2006/0139570 A1 6/2006 Blum et al.
2006/0176572 A1 8/2006 Fiala
2006/0238702 A1 10/2006 Glick et al.
2006/0244904 A1 11/2006 Hong et al.
2006/0244905 A1 11/2006 Piers et al.
2007/0002444 A1 1/2007 Piers et al.
2007/0052920 A1 3/2007 Stewart et al.
2007/0129803 A1 6/2007 Cumming et al.
2007/0171362 A1 7/2007 Simpson et al.
2007/0182924 A1 8/2007 Hong et al.
2007/0236769 A1 10/2007 Zalevsky
2007/0258143 A1 11/2007 Portney
2007/0268451 A1 11/2007 Raghuprasad
2007/0282438 A1 12/2007 Hong et al.
2008/0030677 A1 2/2008 Simpson
2008/0147185 A1 6/2008 Hong et al.
2008/0161913 A1 7/2008 Brady et al.
2008/0161914 A1 7/2008 Brady et al.
2008/0269891 A1 10/2008 Hong et al.
2008/0273169 A1 11/2008 Blum et al.
2008/0300679 A1 12/2008 Altmann
2009/0062911 A1 3/2009 Bogaert
2009/0088840 A1 4/2009 Simpson et al.
2009/0164008 A1 6/2009 Hong et al.
2009/0187242 A1 7/2009 Weeber et al.
2009/0195748 A1 8/2009 Bandhauer et al.
2009/0210054 A1 8/2009 Weeber et al.
2009/0234448 A1 9/2009 Weeber et al.
2009/0240328 A1 9/2009 Treushnikov et al.
2009/0268155 A1 10/2009 Weeber
2009/0268158 A1 10/2009 Weeber
2009/0295295 A1 12/2009 Shannon et al.
2009/0323020 A1 12/2009 Zhao et al.
2010/0014049 A1 1/2010 Bandhauer et al.
2010/0016961 A1 1/2010 Hong et al.
2010/0057202 A1 3/2010 Bogaert
2010/0066973 A1 3/2010 Portney
2010/0087921 A1 4/2010 Simpson
2010/0097569 A1 4/2010 Weeber et al.
2010/0100177 A1 4/2010 Zhao
2010/0100178 A1 4/2010 Weeber et al.
2010/0131060 A1 5/2010 Simpson et al.
2010/0161048 A1 6/2010 Schaper, Jr.
2010/0161051 A1 6/2010 Hong
2010/0274233 A1 10/2010 Dick et al.
2010/0281021 A1 11/2010 Weeber et al.
2010/0312336 A1 12/2010 Hong et al.
2010/0312337 A1 12/2010 Zhang et al.
2010/0321635 A1 12/2010 Apter et al.
2011/0022170 A1 1/2011 Simpson et al.
2011/0098811 A1 4/2011 Hong et al.
2011/0109874 A1 5/2011 Piers et al.
2011/0125261 A1 5/2011 Portney
2011/0149236 A1 6/2011 Weeber
2011/0166652 A1 7/2011 Bogaert et al.
2011/0267693 A1 11/2011 Kobayashi et al.
2011/0270390 A1 11/2011 Kobayashi et al.
2011/0270596 A1 11/2011 Weeber
2011/0292335 A1 12/2011 Schwiegerling
2011/0313522 A1 12/2011 Hayes
2011/0313523 A1 12/2011 Hayes
2011/0313525 A1 12/2011 Cumming
2011/0317124 A1 12/2011 Weeber et al.
2011/0317126 A1 12/2011 Weeber
2012/0029630 A1 2/2012 Piers et al.
2012/0059464 A1 3/2012 Zhao
2012/0140166 A1 6/2012 Zhao
2012/0143326 A1 6/2012 Canovas et al.
2012/0154740 A1 6/2012 Bradley et al.
2012/0165932 A1 6/2012 Argal et al.
2012/0170121 A1 7/2012 Okada et al.
2012/0224138 A1* 9/2012 Cohen .................. A61F 2/1618 623/6.28
2012/0283825 A1 11/2012 Houbrechts et al.
2012/0320335 A1 12/2012 Weeber et al.
2012/0323321 A1 12/2012 Simonov et al.
2013/0035760 A1 2/2013 Portney
2013/0046381 A1 2/2013 Zalevsky et al.
2013/0060330 A1 3/2013 Weeber et al.
2013/0090730 A1 4/2013 Weeber et al.
2013/0107202 A1 5/2013 Liang
2013/0201445 A1 8/2013 Das et al.
2013/0278891 A1* 10/2013 Zhao .................... A61F 2/1618 351/159.78
2014/0168602 A1 6/2014 Weeber
2014/0172088 A1 6/2014 Carson et al.
2015/0022775 A1 1/2015 Ando et al.
2015/0029460 A1 1/2015 Bradley et al.
2015/0094807 A1 4/2015 Piers et al.
2015/0359625 A1 12/2015 Argal et al.
2016/0216535 A1 7/2016 Zhao
2016/0220350 A1 8/2016 Gerlach
2016/0220352 A1 8/2016 Choi et al.
2016/0320633 A1 11/2016 Weeber et al.
2016/0334640 A1 11/2016 De, Jr. et al.
2016/0341978 A1 11/2016 Schwiegerling
2017/0172088 A1 6/2017 May
2017/0209259 A1 7/2017 Choi et al.
2017/0216020 A1 8/2017 Weeber et al.
2017/0219846 A1 8/2017 Ando
2017/0227789 A1 8/2017 Ando et al.
2017/0239038 A1 8/2017 Choi et al.
2017/0245985 A1 8/2017 Canovas et al.
2017/0245986 A1 8/2017 Canovas Vidal et al.
2017/0245987 A1 8/2017 Canovas et al.
2017/0252151 A1 9/2017 Mackool
2018/0092739 A1 4/2018 Pagnoulle et al.
2018/0132996 A1 5/2018 Tiwari et al.
2018/0147050 A1 5/2018 Choi et al.
2018/0147052 A1 5/2018 Hong et al.
2018/0263760 A1 9/2018 Cánovas Vidal et al.
2018/0275428 A1 9/2018 Ando
2018/0368972 A1 12/2018 Rosen et al.
2018/0373060 A1 12/2018 Knox et al.
2019/0004221 A1 1/2019 Weeber et al.
2019/0004331 A1 1/2019 Weeber et al.
2019/0004335 A1 1/2019 Weeber et al.
2019/0224000 A1 7/2019 Choi et al.
2019/0254810 A1 8/2019 Tiwari et al.
2019/0307557 A1 10/2019 De Carvalho et al.

(56) References Cited

U.S. PATENT DOCUMENTS

2019/0314148 A1 10/2019 Liu
2020/0038172 A1 2/2020 Hussain et al.
2021/0196453 A1 7/2021 Rosen et al.
2021/0286196 A1 9/2021 Weeber
2022/0171214 A1 6/2022 Weeber et al.
2022/0244440 A1 8/2022 Weeber et al.
2023/0105462 A1 4/2023 Rosen et al.
2023/0190450 A1 6/2023 Cánovas Vidal et al.

FOREIGN PATENT DOCUMENTS

CA 2507659 A1 6/2004
CA 2590085 A1 6/2006
CN 1951340 A 4/2007
CN 101181171 B 4/2011
CN 102665611 A 9/2012
DE 69715830 T2 8/2003
EP 0037529 A1 10/1981
EP 335731 A2 10/1989
EP 342895 A2 11/1989
EP 0343067 A1 11/1989
EP 0369561 A2 5/1990
EP 375291 A2 6/1990
EP 0393639 A2 10/1990
EP 412751 A2 2/1991
EP 0457553 A2 11/1991
EP 470811 A2 2/1992
EP 605841 A1 7/1994
EP 0316162 B1 10/1995
EP 355230 B1 10/1995
EP 681198 A1 11/1995
EP 0537643 B1 3/1997
EP 0926531 A1 6/1999
EP 949529 A2 10/1999
EP 1376203 A2 1/2004
EP 1424049 A1 6/2004
EP 1862148 A1 12/2007
EP 1310267 B1 1/2008
EP 1891912 A1 2/2008
EP 2043558 A2 4/2009
EP 2045648 A1 4/2009
EP 1402308 B1 5/2009
EP 1424049 B1 6/2009
EP 2103279 A1 9/2009
EP 2113226 A1 11/2009
EP 2334260 A2 6/2011
EP 2365379 A1 9/2011
EP 2377493 A1 10/2011
EP 2378319 A1 10/2011
EP 2290411 B1 5/2012
EP 2363097 B1 9/2012
EP 2590594 A2 5/2013
EP 2812882 A1 12/2014
EP 2813881 A1 12/2014
EP 2349093 B1 10/2015
EP 3150170 B1 12/2017
EP 2527908 B1 3/2019
EP 4487816 A2 1/2025
IT 1215851 B 2/1990
JP H01154119 A 6/1989
JP H0228615 A 1/1990
JP H0279815 A 3/1990
JP H02137814 A 5/1990
JP H02249631 A 10/1990
JP 3011315 A2 1/1991
JP 2000511299 A 8/2000
JP 2003532157 A 10/2003
JP 2010158315 A 7/2010
JP 2013101323 A 5/2013
KR 101154066 B1 6/2012
RU 2011154235 A 7/2013
RU 2011154238 A 7/2013
WO 9002963 A1 3/1990
WO 9222264 A1 12/1992
WO 9303409 A1 2/1993
WO 9413225 A1 6/1994
WO 9417435 A1 8/1994
WO 9724639 A1 7/1997
WO 9744689 A1 11/1997
WO 9831299 A2 7/1998
WO 9907309 A1 2/1999
WO 9923526 A1 5/1999
WO 0019906 A1 4/2000
WO 0076426 A2 12/2000
WO 0121061 A1 3/2001
WO 0163344 A1 8/2001
WO 0182839 A1 11/2001
WO 0189424 A1 11/2001
WO 0221194 A2 3/2002
WO 0234158 A2 5/2002
WO 02084381 A2 10/2002
WO 02088830 A1 11/2002
WO 03009053 A1 1/2003
WO 2004013680 A1 2/2004
WO 2004034129 A1 4/2004
WO 2004049979 A1 6/2004
WO 2004090611 A2 10/2004
WO 2004096014 A2 11/2004
WO 2004113959 A2 12/2004
WO 05019906 A1 3/2005
WO 2005019906 A1 3/2005
WO 06025726 A1 3/2006
WO 2006047698 A1 5/2006
WO 06060477 A2 6/2006
WO 2006060480 A2 6/2006
WO 2006067255 A1 6/2006
WO 2007067872 A2 6/2007
WO 2007092948 A1 8/2007
WO 2007133384 A2 11/2007
WO 2008045847 A2 4/2008
WO 2008150982 A1 12/2008
WO 2009017403 A1 2/2009
WO 2009027438 A2 3/2009
WO 2009043985 A1 4/2009
WO 2009058755 A1 5/2009
WO 2009076670 A1 6/2009
WO 2009130610 A2 10/2009
WO 2009148454 A1 12/2009
WO 2010046356 A1 4/2010
WO 2010054255 A1 5/2010
WO 2010059764 A1 5/2010
WO 2010079528 A1 7/2010
WO 2010093975 A2 8/2010
WO 2010100523 A1 9/2010
WO 2010104530 A1 9/2010
WO 2010144315 A1 12/2010
WO 2011024125 A1 3/2011
WO 2011055228 A2 5/2011
WO 2011075641 A2 6/2011
WO 2011075668 A1 6/2011
WO 2012004746 A2 1/2012
WO 2012031211 A1 3/2012
WO 2012070313 A1 5/2012
WO 2012078763 A1 6/2012
WO 2012085917 A1 6/2012
WO 2012122411 A1 9/2012
WO 2012140389 A1 10/2012
WO 2013018379 A1 2/2013
WO 2013028992 A1 2/2013
WO 2013093916 A1 6/2013
WO 2013114209 A2 8/2013
WO 2013116133 A1 8/2013
WO 2013118177 A1 8/2013
WO 2013118499 A1 8/2013
WO 2014008343 A1 1/2014
WO 2014033543 A2 3/2014
WO 2014091528 A1 6/2014
WO 2014111831 A1 7/2014
WO 2014189049 A1 11/2014
WO 2017137841 A1 8/2017
WO 2017149403 A1 9/2017
WO 2018093873 A1 5/2018
WO 2018100452 A1 6/2018

(56) References Cited

FOREIGN PATENT DOCUMENTS

| | | |
|---|---|---|
| WO | 2018150236 A1 | 8/2018 |
| WO | 2019130030 A1 | 7/2019 |
| WO | 2020115104 A1 | 6/2020 |

OTHER PUBLICATIONS

Alfonso J.F., et al., "Prospective Study of the Acri.LISA Bifocal Intraocular Lens," Journal of Cataract Refractive Surgery, Nov. 2007, vol. 33 (11), pp. 1930-1935.
Alvarez S. L., et al., "Spectral threshold: measurement and clinical applications," British Journal of Ophthalmology, 1983, vol. 67, pp. 504-507.
Apple D.J., et al., Eds., "Intraocular Lenses: Evolution, Designs, Complications and Pathology," in: New Concepts in Intraocular Lens Implantation, Williams & Wilkins publisher, Jan. 1989, vol. 36 (1), pp. 21-36.
Apple D.J., et al., "Intraocular Lenses: Evolution, Designs, Complications and Pathology," New Concepts in Intraocular Lens Implantation, Williams & Wilkins publisher, Jan. 1989, vol. 22 (36), pp. 205-221.
Artal P., et al., "Contributions of the Cornea and the Lens to the Aberrations of the Human Eye," Optics Letters, 1998, vol. 23 (21), pp. 1713-1715.
Atchinson D.A., "Design of Aspheric Intraocular Lens," Ophthamic & Physiological Optics, 1991, vol. 11 (2), pp. 137-146.
Atchinson D.A., et al., "Optical Design of Intraocular Lenses. II. Off-Axis performance," Optometry & Vision Science, 1989, vol. 66 (9), pp. 579-590.
Atchinson D.A., et al., "Third-Order Aberrations of Pseudophakic Eyes," Ophthalmic and Physiological Optics , 1989, vol. 9, pp. 205-211.
Atchinson D.A., "Optical Design of Intraocular Lenses. I. On-Axis Performance," American Academy of Optometry, 1989, vol. 66 (8), pp. 492-506.
Atchinson D.A., "Optical design of intraocular lenses III. On-Axis Performance in the Presence of Lens Displacement," American Academy of Optometry, 1989, vol. 66 (10), pp. 671-681.
Atchinson, "Refractive errors induced by displacement of intraocular lenses within the pseudophakic eye," Optometry & Vision Science, 1989, 66 (3), 146-152.
Bonnet R., et al., "New Method of Topographical Ophthalmometry—Its Theoretical and Clinical Applications," American Journal of Optometry, 1962, vol. 39 (5), pp. 227-251.
Bradley A. et al., "Achromatizing the Human Eye" Optometry & Vision Science, 1991, vol. 68 (8), pp. 608-616.
Buralli D.A., et al., "Optical Performance of Holographic Kinoforms," Applied Optics, Mar. 1989, vol. 28 (5), pp. 976-983.
Canovas C., et al., "Hybrid Adaptive-Optics Visual Simulator," Optical Letters, Jan. 15, 2010, vol. 35 (2), pp. 196-198.
Castignoles F., et al., "Comparison of the Efficiency, MTFand Chromatic Properties of Four Diffractive Bifocal Intraocular Lens Designs," Optics Express, Mar. 2010, vol. 18 (5), pp. 5245-5256.
Cohen A.L., "Diffractive Bifocal Lens Design," Optometry and Vision Science, Jun. 1993, vol. 70 (6), pp. 461-468.
Cohen A.L., "Practical Design of a Bifocal Hologram Contact Lens or Intraocular Lens," Applied Optics, Jul. 1, 1992, vol. 31 (19), pp. 3750-3754.
Diffractive Lenses for Extended Depth of Focus and Presbyopic Correction, Presentation from Wavefront Congress held on Feb. 15, 2008, Rochester, New York.
Doskolovich L.L., et al., "Special Diffractive Lenses," Lens and Optical Systems Design, Apr. 1992, vol. 1780, pp. 393-402.
Dwyer W. O. et al., "Racial Differences in Color Vision: Do They Exist", American Journal of Optometry & Physiological Optics, 1975, 52, 224-229.
El Hage S.G., et al., "Contribution of the Crystalline Lens to the Spherical Aberration of the Eye," 1973, vol. 63 (2), pp. 205-211.
Futhey J.A., "Diffractive Bifocal Intraocular Lens," SPIE, 1989, vol. 1052, pp. 142-148.
Geun Y., et al., "Visual Performance after Correcting the Monchromatic and Chromatic Aberrations of the Eye," Journal of the Optical Society of America, 2002, vol. 19 (2), pp. 266-275.
Glasser A et al., "Presbyopia and the optical changes in the human crystalline lens with age," Vision Res, 1998, 38 (2), 209-229.
Greivenkamp J.E., et al., "Visual Acuity Modeling Using Optical Raytracing Of Schematic Eyes," American Journal of Ophthalmology, 1995, vol. 120 (2), pp. 227-240.
Griswold Scott et al., "Scotopic Spectral Sensitivity of Phakic and Aphakic Observers Extending into the Near Ultraviolet," Vision res, 1992, 32 (9), 1739-1743.
Guirao A., et al., "Corneal Wave Aberration from Videokeratography: Accuracy and Limitations of the Procedure," Journal of the Optical Society of America, 2000, vol. 17 (6), pp. 955-965.
IOVS, 1999, 40 (4), S535.
Kiely et al., "The mean shape of the human cornea," Optica ACTA, 1982, 29 (8), 1027-1040.
Kokoschka S., et al., "Influence of Field Size on the Spectral Sensitivity of the Eye in the Photopic and Mesopic Range," American Journal of Optometry and Physiological Optics, 1985, vol. 62 (2), pp. 119-126.
Liang J., et al., "Objective Measurement of Wave Aberrations of the Human Eye With the Use of a Hartmann-Shack Wave-Front Sensor," Journal of the Optical Society of America, 1994, vol. 11 (7), pp. 1949-1957.
Lindsay R., et al., "Descriptors of Corneal Shape," Optometry and Vision Science, 1998, vol. 75 (2), pp. 156-158.
Liou H.L., et al., "Anatomically Accurate, Finite Model Eye for Optical Modeling," Journal of Optical Society of America, Aug. 1997, vol. 14 (8), pp. 1684-1695.
Lotmar, "Theoretical eye model with aspherics," Journal of the Optical Society of America, 1971, 61 (11), 1522-1529.
Malacara D., et al., "Wavefront Fitting With Discrete Orthogonal Polynomials in a Unit Radius Circle," Optical Engineering, 1990, vol. 29 (6), pp. 672-675.
Mandell R.B., et al., "Mathematical Model of the Corneal Contour," 1965, School of Optometry, University of California, Berkeley, pp. 183-197.
Marcos S., et al., "A New Approach to the Study of Ocular Chromatic Aberrations," Vision Research, 1999, vol. 39 (26), pp. 4309-4323.
Marsack J.D., et al., "Metrics of Optical Quality Derived from Wave Aberrations Predict Visual Performance," Journal of Vision, Apr. 2004, vol. 4 (4), pp. 322-328.
Monsoriu J.A., et al., "Devil's Lenses," Optics Express, Oct. 17, 2007, vol. 15 (21), pp. 13858-13864.
Mordi J.A., et al., "Influence of Age of Chromatic Aberration of the Human Eye," American Journal of Optometry & Physiological Optics, 1985, vol. 62 (12), pp. 864-869.
Morlock, R., et al., "Patient-Reported Spectacle Independence Questionnaire (PRSIQ): Development and Validation," American Journal of Ophthalmology, Jun. 2017, vol. 178, pp. 101-114.
Navarro R., et al., "Accommodation-Dependent Model of the Human Eye with Aspherics," Journal of the Optical Society of America, Aug. 1985, vol. 2 (8), pp. 1273-1281.
Norrby S., et al., "Model Eyes for Evaluation of Intraocular Lenses," Applied Optics, Sep. 7, 2007, vol. 46 (26), pp. 6595-6605.
"Optical Design," Military Standardization Handbook, 1962, Chapter 4, U.S. Department of Defense MIL-HDBK-141, 4-1-4-19.
Oshika T., et al., "Changes in Corneal Wavefront Aberrations with Aging," Investigative Ophthalmology & Visual Science, 1999, vol. 40 (7), pp. 1351-1355.
Patel S., et al., "Shape and Radius of Posterior Corneal Surface," Refractive and Corneal Surgery, 1993, vol. 9 (3), pp. 173-181.
PIERS P.A., et al., "Eye Models for the Prediction of Contrast Vision in Patients with New Intraocular Lens Designs," Optics Letters, Apr. 1, 2004, vol. 29 (7), pp. 733-735.
Piers P.A., et al., "Theoretical Comparison of Aberration-Correcting Customized and Aspheric Intraocular Lenses," Journal of Refractive Surgery, Apr. 2007, vol. 23 (4), pp. 374-384.

(56) References Cited

OTHER PUBLICATIONS

Alarcon et al., "Preclinical Metrics to Predict through-focus Visual Acuity for Pseudophakic Patients", Biomedical Optics Express, vol. 7, No. 5, pp. 1877-1888, 2016.
Guillon et al., "Corneal Topography: A Clinical Model", Ophthalmic & Physiological Optics, vol. 6, No. 1, pp. 47-56, 1986.
IOVS, "Corneal Aberrations and Quality of Vision after Refractive Surgery II", vol. 40, No. 4, S545, 1 page, Mar. 15, 1999.
ISO 11979-2, "Part 2—Optical Properties and Test Methods—Ophthalmic Implants—Intraocular Lenses", International Organization for Standardization, Edition 2, 30 pages, Aug. 15, 2014.
Smith et al., "The Spherical Aberration of Intra-ocular Lenses", Ophthalmic & Physiological Optics: The Journal of the British College of Ophthalmic Opticians (Optometrists), vol. 8, No. 3, pp. 287-294, 1988.
Watson et al., "A Unified Formula for Light-adapted Pupil Size", Journal of Vision, vol. 12, No. 10, pp. 1-16, Sep. 25, 2012.
Said et al., "The Variation with Age of the Spectral Transmissivity of the Living Human Crystalline Lens," Gerontologia, 1959, 213-231.
Schwiegerling et al., "Representation of videokeratoscopic height data with Zernike polynomials," Journal of the Optical Society of America, 1995, 12 (10), 2105-2113.
Seitz B., et al., "Corneal Topography," Current Opinion in Ophthalmolgy, 1997, vol. 8 (4), pp. 8-24.
Siedlecki D., et al., "Radial Gradient index Intraocular Lens: a Theoretical Model," Journal of Modern Optics, Feb. 20-Mar. 10, 2008, vol. 55 (4-5), pp. 639-647.
Smith G., et al., "The Spherical Aberration of the Crystalline Lens of the Human Eye," Vision Res., 2001, vol. 41 (2), pp. 235-243.
Smith Kinney, "Sensitivity of the eye to spectral radiation at scotopic and mesopic intensity levels," Journal of the Optical Society of America, 1955, 45 (7), 507-514.
Sokołowski M., et al. "Hybrid Heptafocal Intraocular Lenses," Optica Applicata, Dec. 2015, vol. 45(3), pp. 285-298.
Terwee T., et al., "Visualization of the Retinal Image in an Eye Model With Spherical and Aspheric, Diffractive, and Refractive Multifocal Intraocular Lenses," Journal of Refractive Surgery, Mar. 2008, vol. 24 (3), pp. 223-232.
Thibos L. N. et al., "The chromatic eye: a new reduced-eye model of ocular chromatic aberration in humans," Applied Optics, 1992, 31 (19), 3594-3600.
Thibos L. N. et al., "Theork and measurement of ocular chromatic aberration," Vision Res, 1988, 30 (1), 33-49.
Townsley, "New Knowledge of the corneal contour," Contacto, 1970, pp. 38-43.
Van Den Berg T.J., "Analysis of Intraocular Straylight, Especially in Relation to Age," Optometry and Vision Science, Feb. 1995, vol. 72 (2), pp. 52-59.
Van Meeteren A., "Calculations on the Optical Modulation Transfer Function of the Human Eye for White Light," Optica Acta, May 1974, vol. 21 (5), pp. 395-412.
Verriest G., "The Spectral Curve of Relative Luminous Efficiency in Different Age Groups of Aphakic Eyes," Mod Probl Ophthalmol., 1974, 13, 314-317.
Mllegas E.A., et al., "Correlation between Optical and Psychophy, Sical Parameters as a Function of Defocus," Optometry and Vision Science, Jan. 1, 2002, vol. 79 (1), pp. 60-67.
Wang J.Y., et al., "Wave-Front Interpretation With Zernike Polynomials," Applied Optics, 1980, vol. 19 (9), pp. 1510-1518.
U.S. Appl. No. 18/052,853, titled, "Diffractive intraocular lenses for extended range of vision," filed Nov. 4, 2022.

* cited by examiner 500
502
504
506
508
510
512
514
516
518
520a
520b
522a
522b
524a
524b
526
528
530
532
534
536
538
540
542a
542b
544a
544b
546a
546b
548
550
Profile height
Radial coordinate (mm)
0.5
1
1.5
2
2.5
3

600
602
604
606
608
610
612
614
616
618
620a
620b
622a
622b
624a
624b
626
628
630
632
634
636
638
640
642a
642b
644a
644b
646a
646b
648
650
Profile height
Radial coordinate (mm)
0.5
1
1.5
2
2.5
3

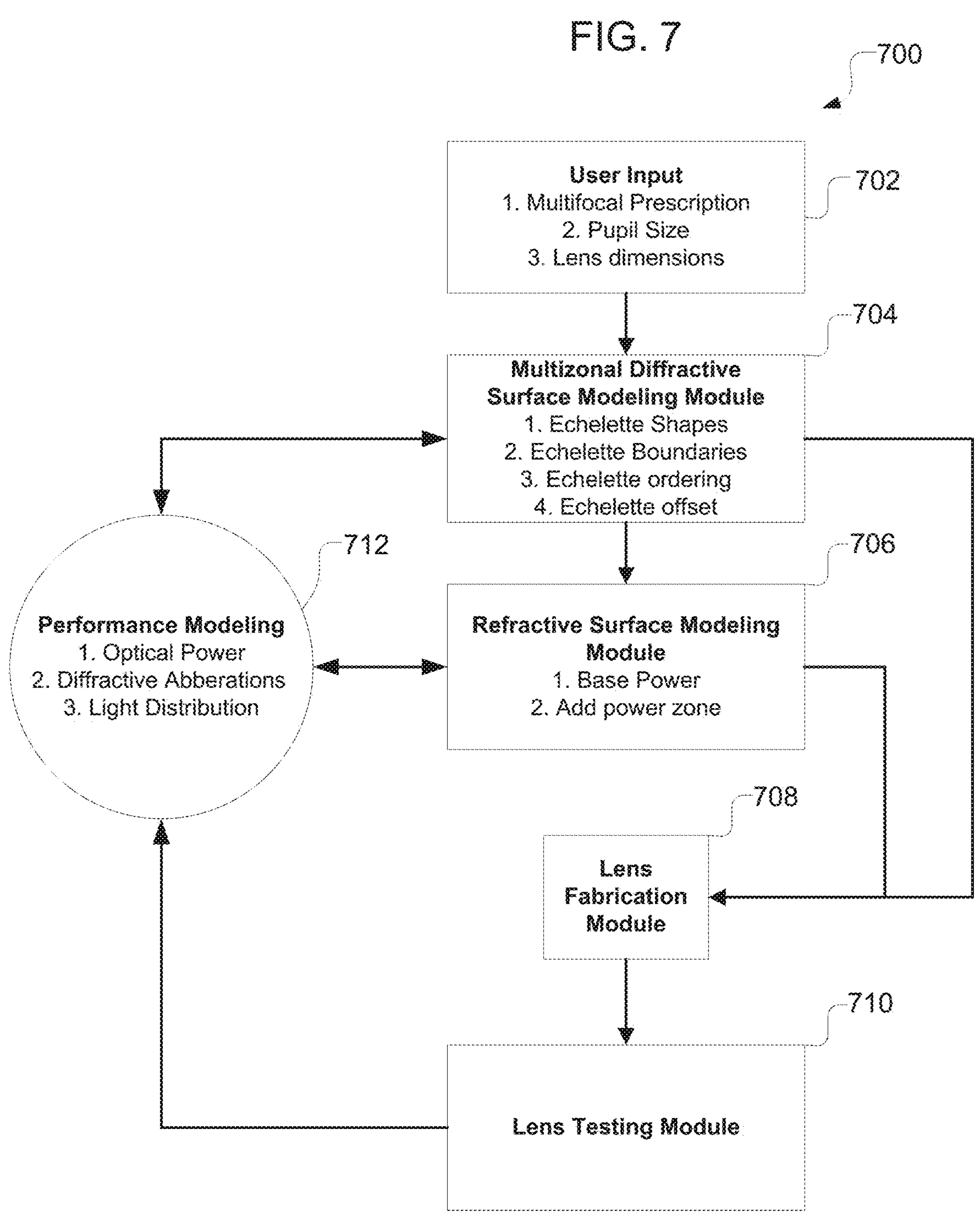
FIG. 7
700
User Input
1. Multifocal Prescription
2. Pupil Size
3. Lens dimensions
702
704
Multizonal Diffractive Surface Modeling Module
1. Echelette Shapes
2. Echelette Boundaries
3. Echelette ordering
4. Echelette offset
712
706
Performance Modeling
1. Optical Power
2. Diffractive Abberations
3. Light Distribution
Refractive Surface Modeling Module
1. Base Power
2. Add power zone
708
Lens Fabrication Module
710
Lens Testing Module

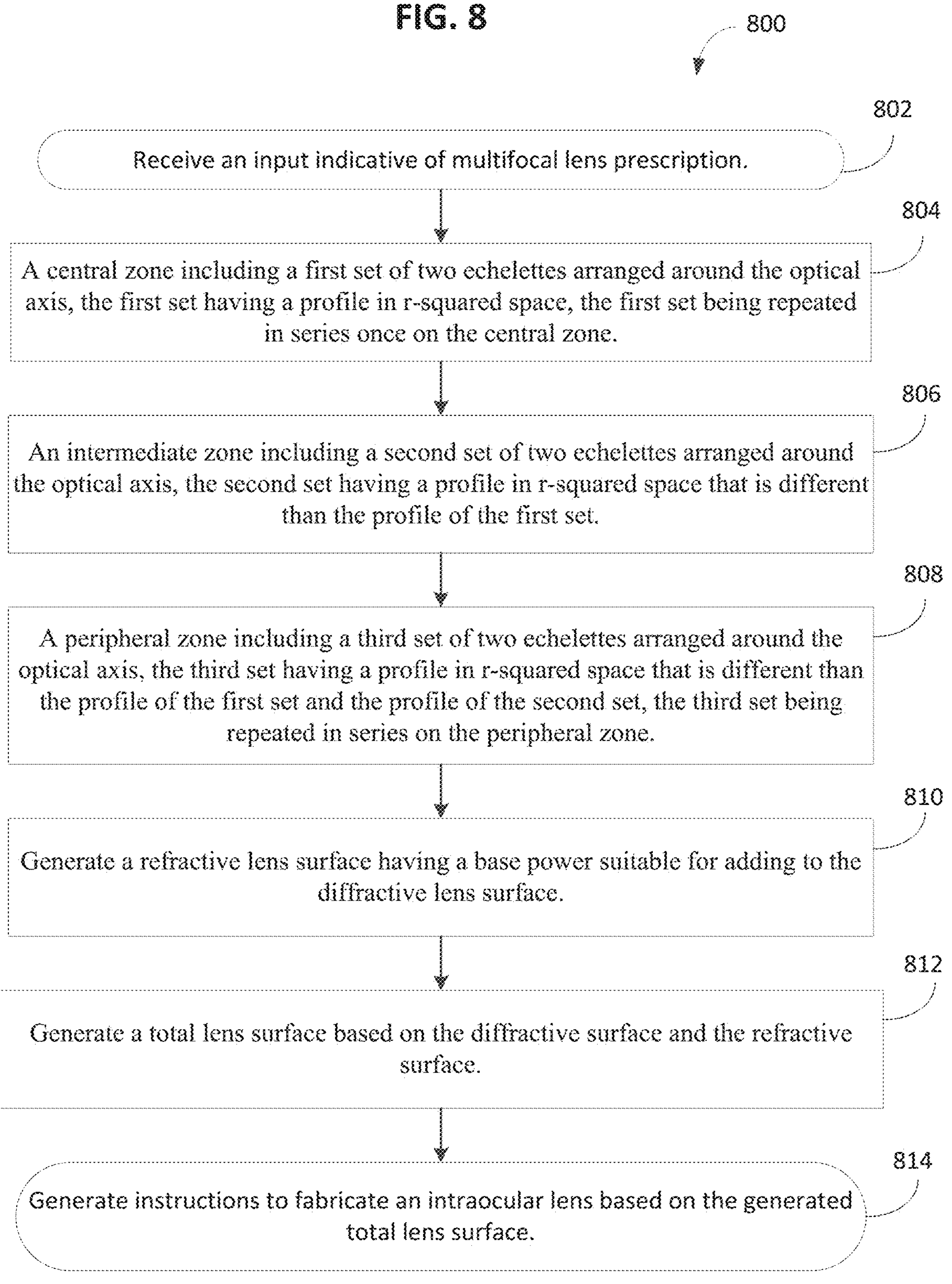
FIG. 8
800
802
Receive an input indicative of multifocal lens prescription.
804
A central zone including a first set of two echelettes arranged around the optical axis, the first set having a profile in r-squared space, the first set being repeated in series once on the central zone.
806
An intermediate zone including a second set of two echelettes arranged around the optical axis, the second set having a profile in r-squared space that is different than the profile of the first set.
808
A peripheral zone including a third set of two echelettes arranged around the optical axis, the third set having a profile in r-squared space that is different than the profile of the first set and the profile of the second set, the third set being repeated in series on the peripheral zone.
810
Generate a refractive lens surface having a base power suitable for adding to the diffractive lens surface.
812
Generate a total lens surface based on the diffractive surface and the refractive surface.
814
Generate instructions to fabricate an intraocular lens based on the generated total lens surface.

INTRAOCULAR LENSES FOR PRESBYOPIA TREATMENT

CROSS REFERENCE TO RELATED APPLICATIONS

The present application is a divisional of and claims priority to U.S. patent application Ser. No. 16/015,119, filed Jun. 21, 2018, which claims the benefit of U.S. Provisional Application No. 62/524,128, filed Jun. 23, 2017, the entire contents of which are incorporated herein by reference.

BACKGROUND

Embodiments of the present disclosure relate generally to diffractive ophthalmic lenses, and particular embodiments provide methods, devices, and systems for mitigating or treating vision conditions such as presbyopia, often by determining a desired multifocal power profile and selecting a geometry of the diffractive profile that results in a diffractive lens shape according to the desired power profile and to various parameters of the patient's eye. Embodiments also relate to vision treatment techniques and in particular embodiments, to ophthalmic lenses such as, for example, contact lenses, corneal inlays or onlays, or intraocular lenses (IOLs) including, for example, phakic IOLs and piggyback IOLs (i.e. IOLs implanted in an eye already having an IOL).

Presbyopia is a condition that affects the accommodation properties of the eye. As objects move closer to a young, properly functioning eye, the effects of ciliary muscle contraction and zonular relaxation allow the lens of the eye to change shape, and thus increase its optical power and ability to focus at near distances. This accommodation can allow the eye to focus and refocus between near and far objects.

Presbyopia normally develops as a person ages, and is associated with a natural progressive loss of accommodation. The presbyopic eye often loses the ability to rapidly and easily refocus on objects at varying distances. The effects of presbyopia usually become noticeable after the age of 45 years. By the age of 65 years, the crystalline lens has often lost almost all elastic properties and has only limited ability to change shape.

Along with reductions in accommodation of the eye, age may also induce clouding of the lens due to the formation of a cataract. A cataract may form in the hard central nucleus of the lens, in the softer peripheral cortical portion of the lens, or at the back of the lens. Cataracts can be treated by the replacement of the cloudy natural lens with an artificial lens. An artificial lens replaces the natural lens in the eye, with the artificial lens often being referred to as an intraocular lens or "IOL".

Multifocal IOLs may, for example, rely on a diffractive optical surface to direct portions of the light energy toward differing focal distances, thereby allowing the patient to clearly see both near and far objects. Multifocal ophthalmic lenses (including contact lenses or the like) have also been proposed for treatment of presbyopia without removal of the natural crystalline lens. Diffractive optical surfaces, either monofocal or multifocal, may also be configured to provide reduced chromatic aberration.

Diffractive monofocal and multifocal lenses can make use of a material having a given refractive index and a surface curvature which provide a refractive power. Diffractive lenses have a diffractive profile which confers the lens with a diffractive power that contributes to the overall optical power of the lens. The diffractive profile is typically characterized by a number of diffractive zones. When used for ophthalmic lenses these diffractive zones are typically annular lens zones, or echelettes, spaced about the optical axis of the lens. Each echelette may be defined by an optical zone, a transition zone between the optical zone and an optical zone of an adjacent echelette, and echelette geometry. The echelette geometry includes an inner and outer diameter and a shape or slope of the optical zone, a height or step height, and a shape of the transition zone. The surface area or diameter of the echelettes largely determines the diffractive power(s) of the lens and the step height of the transition between echelettes largely determines the light distribution between the different add powers. Together, these echelettes form a diffractive profile.

A multifocal diffractive profile of the lens may be used to mitigate presbyopia by providing two or more optical powers; for example, one for near vision and one for far vision. The lenses may also take the form of an intraocular lens placed within the capsular bag of the eye, replacing the original lens, or placed in front of the natural crystalline lens. The lenses may be in the form of a contact lens, most commonly a bifocal contact lens, or in any other form mentioned herein.

Multifocal (e.g. diffractive) intraocular lenses (IOLs) are intended to provide a patient with improved vision at different distances, such as near, intermediate and far. The near vision may generally correspond to vision provided when objects are at a distance of equal or less than 1.5 feet from a subject eye. Intermediate vision may generally correspond to vision for objects at a distance between about 1½ feet and about 5-6 feet from a subject eye. Far vision may generally correspond to vision for objects at any distance greater than about 5-6 feet from a subject eye. Such characterizations of near, intermediate, and far vision correspond to those addressed in Morlock R, Wirth R J, Tally S R, Garufis C, Heichel C W D, Patient-Reported Spectacle Independence Questionnaire (PRSIQ): Development and Validation. Am J Ophthalmology 2017; 178:101-114.

Since multifocal IOLs provide multiple focal lengths, the focused image on the retina originating from the focal length that corresponds to the particular viewing distance is overlapping with unfocused images originating from the other focal lengths. This can create visual artifacts for the patient. Furthermore, conventional approaches typically provide for near and far vision, but achieve unsatisfactory visual performance at intermediate distances. Relatedly, increasing the number of focal lengths in an IOL can exacerbate the aforementioned visual artifacts. Therefore, multifocal conventional ophthalmic approaches may fail to adequately improve visual performance at intermediate distances.

BRIEF SUMMARY

Embodiments herein described include an ophthalmic lens with a first surface and a second surface disposed about an optical axis, and a diffractive profile imposed on one of the first surface or the second surface. The diffractive profile may include a central zone, a peripheral zone, and a middle zone positioned between the central zone and the peripheral zone. The central zone may include a first set of two echelettes arranged around the optical axis, the first set having a profile in r-squared space, the first set being repeated in series at least once on the central zone. The middle zone may include a second set of two echelettes arranged around the optical axis, the second set having a profile in r-squared space that is different than the profile of the first set. The peripheral zone may include a third set of two echelettes arranged around the optical axis, the third set having a profile in r-squared space that is different than the profile of the first set and the profile of the second set, the third set being repeated in series at least once on the peripheral zone.

Embodiments herein described include an ophthalmic lens including a first surface and a second surface disposed about an optical axis. A diffractive profile is imposed on one of the first surface or the second surface. The diffractive profile includes a first set of two echelettes arranged around the optical axis, the first set having a profile in r-squared space, the first set being repeated to form a first repeated set. The diffractive profile includes a second set of two echelettes arranged around the optical axis, the second set being adjacent the first repeated set, the second set having a profile in r-squared space that is different than the profile of the first set. The diffractive profile includes a third set of two echelettes arranged around the optical axis, the third set being adjacent the second set, the third set having a profile in r-squared space that is different than the profile of the first set and the profile of the second set, the third set being repeated to form a second repeated set.

Embodiments herein described include an ophthalmic lens including a first surface and a second surface disposed about an optical axis. A diffractive profile is imposed on one of the first surface or the second surface. The diffractive profile includes a central zone and a peripheral zone. The central zone includes a first set of two echelettes arranged around the optical axis, the first set having a profile in r-squared space, the first set being repeated in series at least once on the central zone. The peripheral zone includes a second set of two echelettes arranged around the optical axis, the second set having a profile in r-squared space that is different than the profile of the first set, the second set being repeated in series at least once on the peripheral zone.

Embodiments herein described also include manufacturing systems for making an ophthalmic lens. Such manufacturing system can include an input that accepts an ophthalmic lens prescription for a patient eye. A first module is configured to generate a diffractive profile based on the ophthalmic lens prescription. The diffractive profile includes a central zone, a peripheral zone, and a middle zone positioned between the central zone and the peripheral zone. The central zone includes a first set of two echelettes arranged around an optical axis, the first set having a profile in r-squared space, the first set being repeated in series at least once on the central zone. The middle zone includes a second set of two echelettes arranged around the optical axis, the second set having a profile in r-squared space that is different than the profile of the first set. The peripheral zone includes a third set of two echelettes arranged around the optical axis, the third set having a profile in r-squared space that is different than the profile of the first set and the profile of the second set, the third set being repeated in series at least once on the peripheral zone. The manufacturing system includes a manufacturing assembly that fabricates the ophthalmic lens based on the diffractive profile.

Embodiments herein described also include manufacturing systems for making an ophthalmic lens. Such manufacturing system can include an input that accepts an ophthalmic lens prescription for a patient eye. A first module is configured to generate a diffractive profile based on the ophthalmic lens prescription. The diffractive profile includes a central zone and a peripheral zone. The central zone includes a first set of two echelettes arranged around an optical axis, the first set having a profile in r-squared space, the first set being repeated in series at least once on the central zone. The peripheral zone includes a second set of two echelettes arranged around the optical axis, the second set having a profile in r-squared space that is different than the profile of the first set, the second set being repeated in series at least once on the peripheral zone. The manufacturing system includes a manufacturing assembly that fabricates the ophthalmic lens based on the diffractive profile.

Embodiments herein described also include methods of designing an intraocular lens. Such methods can include defining a diffractive profile and generating a diffractive lens surface based on the diffractive profile. The diffractive profile may include a central zone, a peripheral zone, and a middle zone positioned between the central zone and the peripheral zone. The central zone includes a first set of two echelettes arranged around the optical axis, the first set having a profile in r-squared space, the first set being repeated in series at least once on the central zone. The middle zone includes a second set of two echelettes arranged around the optical axis, the second set having a profile in r-squared space that is different than the profile of the first set. The peripheral zone includes a third set of two echelettes arranged around the optical axis, the third set having a profile in r-squared space that is different than the profile of the first set and the profile of the second set, the third set being repeated in series at least once on the peripheral zone.

Embodiments herein described also include methods of designing an intraocular lens. Such methods can include defining a diffractive profile and generating a diffractive lens surface based on the diffractive profile. The diffractive profile may include a central zone and a peripheral zone. The central zone includes a first set of two echelettes arranged around an optical axis, the first set having a profile in r-squared space, the first set being repeated in series at least once on the central zone. The peripheral zone includes a second set of two echelettes arranged around the optical axis, the second set having a profile in r-squared space that is different than the profile of the first set, the second set being repeated in series at least once on the peripheral zone.

BRIEF DESCRIPTION OF THE DRAWINGS

FIG. 7 is a simplified block diagram illustrating a system for generating a diffractive lens surface, in accordance with embodiments;

FIG. 8 illustrates an example process for generating a diffractive lens surface.

DETAILED DESCRIPTION

Contemporary Lens Shapes and Diffractive Profiles

FIGS. 1A, 1B, 2A, 2B, 3A, and 3B, illustrate multifocal IOL lens geometries, aspects of which are described in U.S. Patent Publication No. 2014-0168602 A1 and U.S. Patent Publication No. 2011-0149236 A1, which are hereby incorporated by reference in their entireties.

Figure 1A:
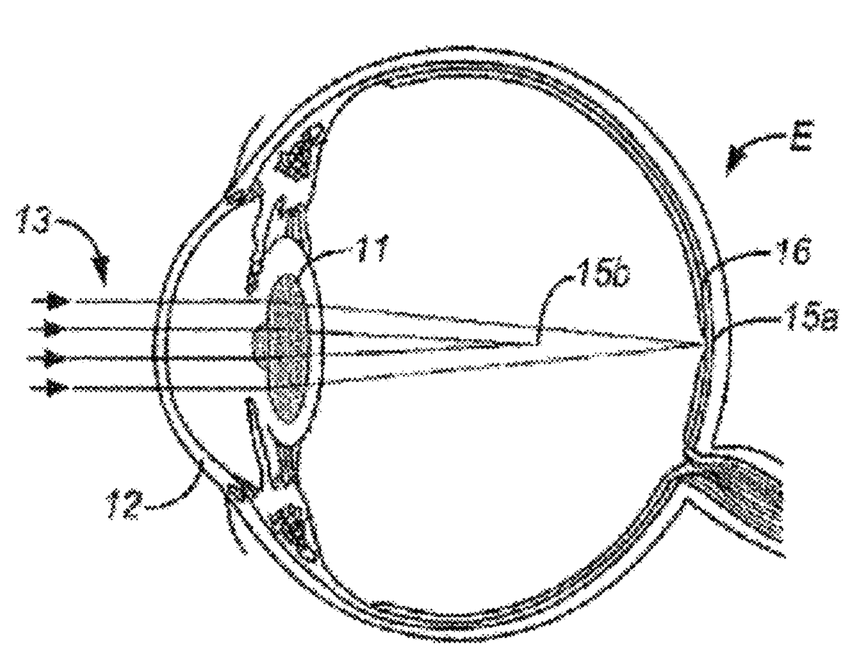
FIG. 1A illustrates a cross-sectional view of an eye with an implanted multifocal refractive intraocular lens.

FIG. 1A is a cross-sectional view of an eye E fit with a multifocal IOL 11. As shown, multifocal IOL 11 may, for example, comprise a bifocal IOL. Multifocal IOL 11 receives light from at least a portion of cornea 12 at the front of eye E and is generally centered about the optical axis of eye E. For ease of reference and clarity, FIGS. 1A and 1B do not disclose the refractive properties of other parts of the eye, such as the corneal surfaces. Only the refractive and/or diffractive properties of the multifocal IOL 11 are illustrated.

Each major face of lens 11, including the anterior (front) surface and posterior (back) surface, generally has a refractive profile, e.g. biconvex, plano-convex, plano-concave, meniscus, etc. The two surfaces together, in relation to the properties of the surrounding aqueous humor, cornea, and other optical components of the overall optical system, define the effects of the lens 11 on the imaging performance by eye E. Conventional, monofocal IOLs have a refractive power based on the refractive index of the material from which the lens is made, and also on the curvature or shape of the front and rear surfaces or faces of the lens.

Multifocal lenses may optionally also make special use of the refractive properties of the lens. Such lenses generally include different powers in different regions of the lens so as to mitigate the effects of presbyopia. For example, as shown in FIG. 1A, a perimeter region of refractive multifocal lens 11 may have a power which is suitable for viewing at far viewing distances. The same refractive multifocal lens 11 may also include an inner region having a higher surface curvature and a generally higher overall power (sometimes referred to as a positive add power) suitable for viewing at near distances.

Figure 1B:
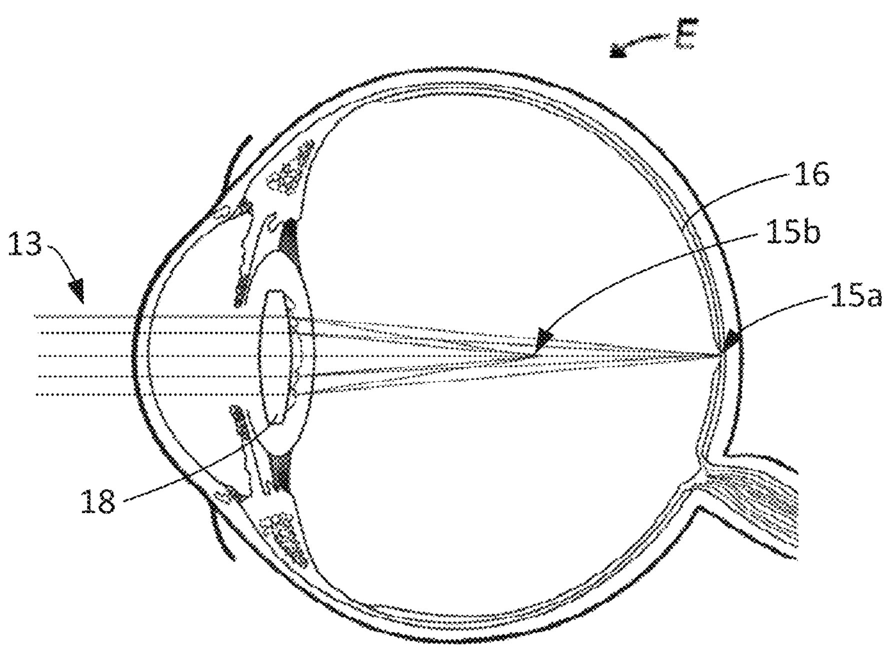
FIG. 1B illustrates a cross-sectional view of an eye having an implanted multifocal diffractive intraocular lens.

Rather than relying entirely on the refractive properties of the lens, multifocal diffractive IOLs or contact lenses can also have a diffractive power, as illustrated by the IOL 18 shown in FIG. 1B. The diffractive power can, for example, comprise positive or negative power, and that diffractive power may be a significant (or even the primary) contributor to the overall optical power of the lens. The diffractive power is conferred by a plurality of concentric diffractive zones which form a diffractive profile. The diffractive profile may either be imposed on the anterior face or posterior face or both.

The diffractive profile of a diffractive multifocal lens directs incoming light into a number of diffraction orders. As light enters from the front of the eye, the multifocal lens 18 directs light to form a far field focus 15*a* on retina for viewing distant objects and a near field focus 15*b* for viewing objects close to the eye. Depending on the distance from the source of light 13, the focus on retina 16 may be the near field focus 15*b* instead. Typically, far field focus 15*a* is associated with $0^{th}$ diffractive order and near field focus 15*b* is associated with the $1^{st}$ diffractive order, although other orders may be used as well as seen in embodiments below.

Bifocal ophthalmic lens 18 typically distributes the majority of light energy into two viewing orders, often with the goal of splitting imaging light energy between the 2 viewing orders about evenly (50%:50%), one viewing order corresponding to far vision and one viewing order corresponding to near vision, although typically, some fraction goes to non-viewing orders.

Corrective optics may be provided by phakic IOLs, which can be used to treat patients while leaving the natural lens in place. Phakic IOLs may be angle supported, iris supported, or sulcus supported. The phakic IOL can be placed over the natural crystalline lens or piggy-backed over another IOL. It is also envisioned that the present disclosure may be applied to inlays, onlays, accommodating IOLs, spectacles, and even laser vision correction.

Figures 2A, 2B:
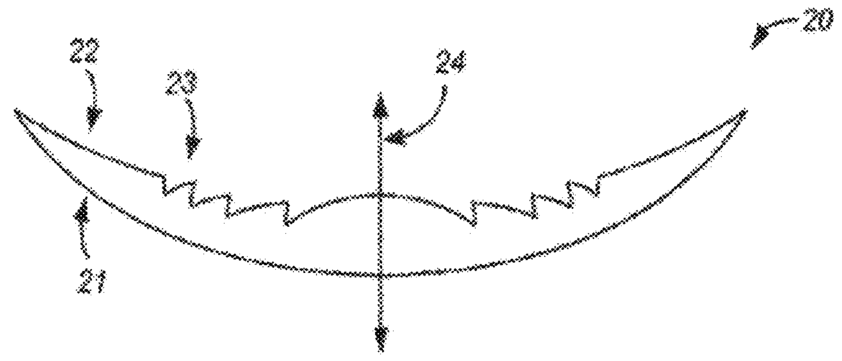
FIG. 2A illustrates a front view of a diffractive multifocal intraocular lens.
FIG. 2B illustrates a cross-sectional view of a diffractive multifocal intraocular lens.

FIGS. 2A and 2B show aspects of a conventional diffractive multifocal lens 20. Multifocal lens 20 may have certain optical properties that are generally similar to those of multifocal IOLs 11, 18 described above. Multifocal lens 20 has an anterior lens face 21 and a posterior lens face 22 disposed about optical axis 24.

When fitted onto the eye of a subject or patient, the optical axis of lens 20 is generally aligned with the optical axis of eye E. The curvature of lens 20 gives lens 20 an anterior refractive profile and a posterior refractive profile. Although a diffractive profile may also be imposed on either anterior face 21 and posterior face 22 or both, FIG. 2B shows posterior face 22 with a diffractive profile. The diffractive profile is characterized by a plurality of annular diffractive zones or echelettes 23 spaced about optical axis 24. While analytical optics theory generally assumes an infinite number of echelettes, a standard multifocal diffractive IOL typically has at least 9 echelettes, and may have over 30 echelettes. For the sake of clarity, FIG. 2B shows only 4 echelettes. Typically, an IOL is biconvex, or possibly plano-convex, or convex-concave, although an IOL could be plano-plano, or other refractive surface combinations.

Figure 3A:
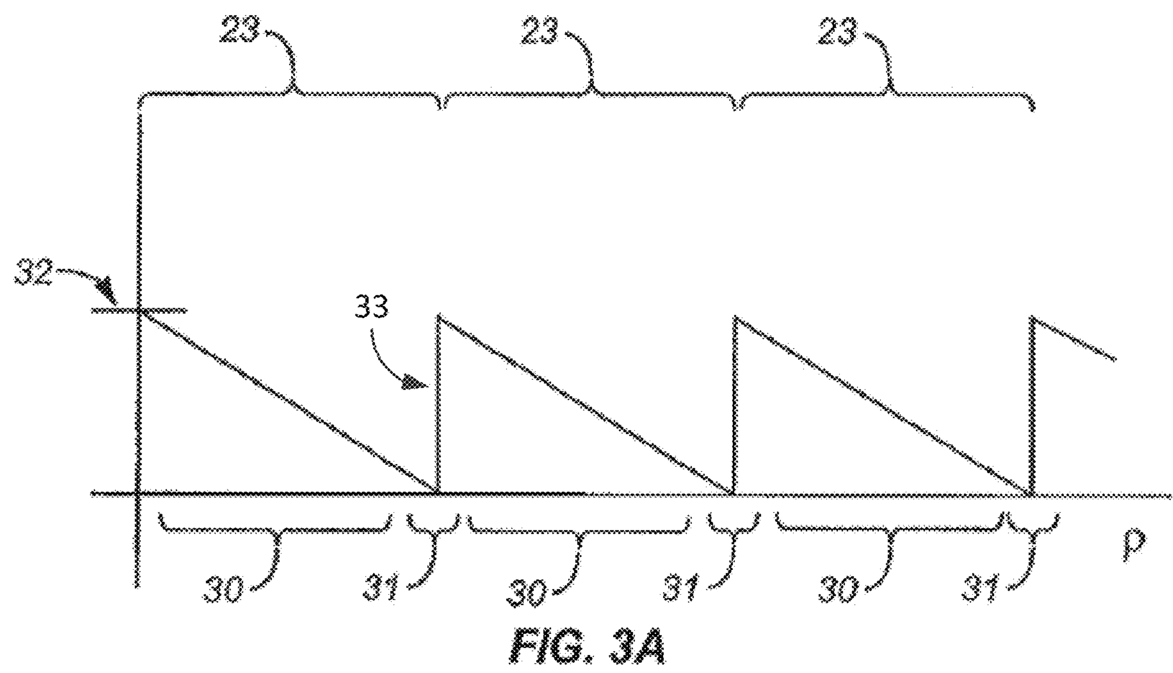
FIGS. 3A and 3B are graphical representations of a portion of the diffractive profile of a conventional diffractive multifocal lens.
Figure 3B:
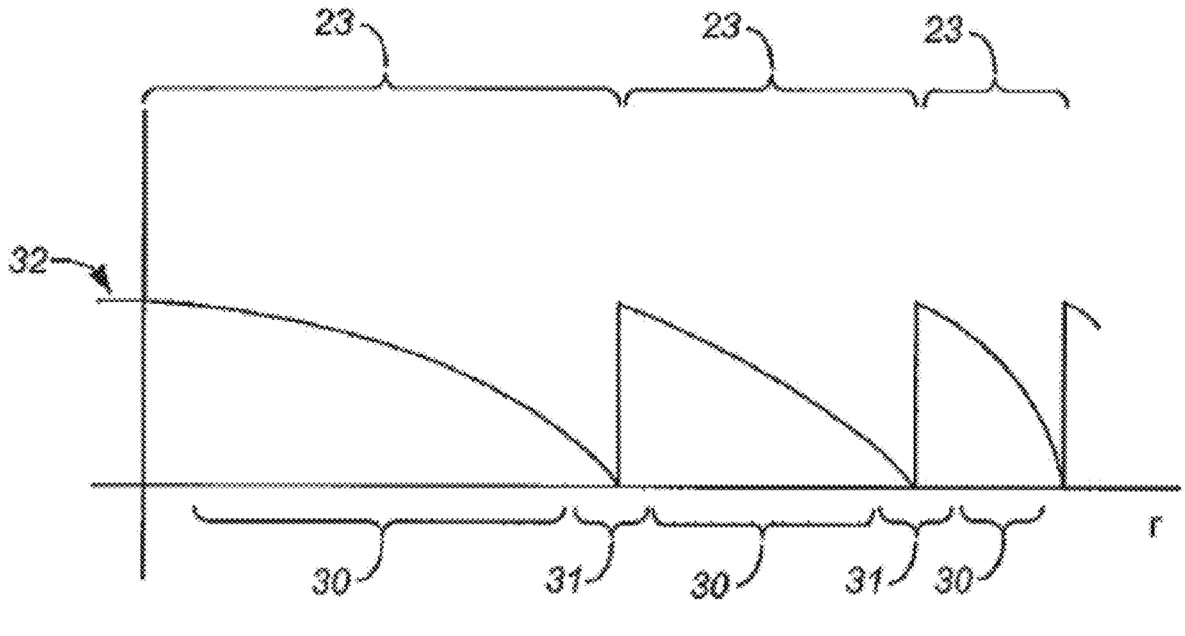

FIGS. 3A and 3B are graphical representations of a portion of a typical diffractive profile of a multifocal lens. While the graph shows only 3 echelettes, typical diffractive lenses extend to at least 9 echelettes to over 32 echelettes. In FIG. 3A, the height 32 of the surface relief profile (from a plane perpendicular to the light rays) of each point on the echelette surface is plotted against the square of the radial distance ($r^2$ or ρ) from the optical axis of the lens (referred to as r-squared space). In multifocal lenses, each echelette 23 may have a diameter or distance from the optical axis which is often proportional to $\sqrt{n}$, n being the number of the echelette 23 as counted from optical axis 24. Each echelette has a characteristic optical zone 30 and transition zone 31. Optical zone 30 typically has a shape or downward slope that is parabolic as shown in FIG. 3B. The slope of each echelette in r-squared space (shown in FIG. 3A), however, is the same. As for the typical diffractive multifocal lens, as shown here, all echelettes have the same surface area. The area of echelettes 23 determines the diffractive power of lens 20, and, as area and radii are correlated, the diffractive power is also related to the radii of the echelettes. The physical offset of the trailing edge of each echelette to the leading edge of the adjacent echelette is the step height. An exemplary step height between adjacent echelettes is marked as reference number 33 in FIG. 3A. The step heights remain the same in r-squared space (FIG. 3A) and in linear space (FIG. 3B). The step offset is the height offset of the transition zone from the underlying base curve. An exemplary step offset is marked as reference number 526 in FIG. 5.

Conventional multifocal diffractive lenses typically provide for near and far vision, neglecting visual performance at intermediate distances. It is possible to produce a lens having a far focal length, an intermediate focal length and a near focal length by having repeated sets of two echelettes that focus light to different focal lengths. This can help to improve the visual performance at intermediate distances. However, as the number of optical zones increases, the risk of visual artifacts also increases. For example, in a trifocal diffractive lens having near, intermediate, and far focal lengths, light from the near focal length may be visible, albeit out of focus, to a user looking at an object in the intermediate or far distance.

Figure 4:
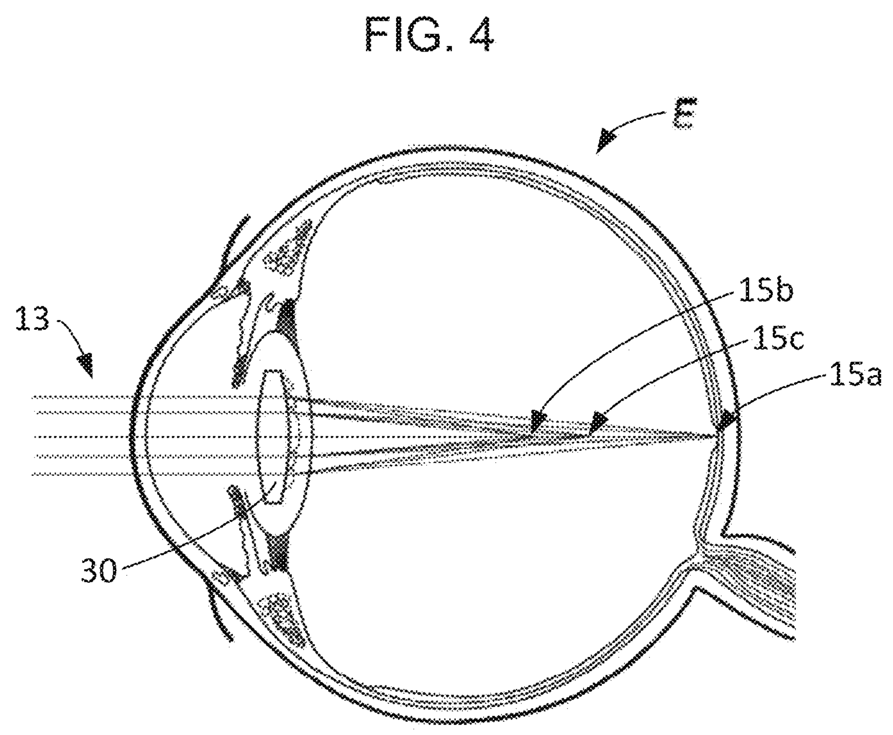
FIG. 4 illustrates a cross-sectional view of an eye having an implanted multifocal diffractive intraocular lens having a far, a near, and an intermediate focal length.

FIG. 4 shows a diffractive multifocal IOL 30 having a third, intermediate focal length 15*c*. The addition of the third, intermediate focal length 15*c* can increase the performance of the IOL 30 for users by providing improved visual acuity at the intermediate distances, i.e. for viewing objects in the range of about 1.5 feet to about 5-6 feet from the eye. The diffractive profile of the diffractive multifocal IOL 30 may be configured to possess additional focal lengths beyond the near focal length and far focal lengths described above.

Figure 5:
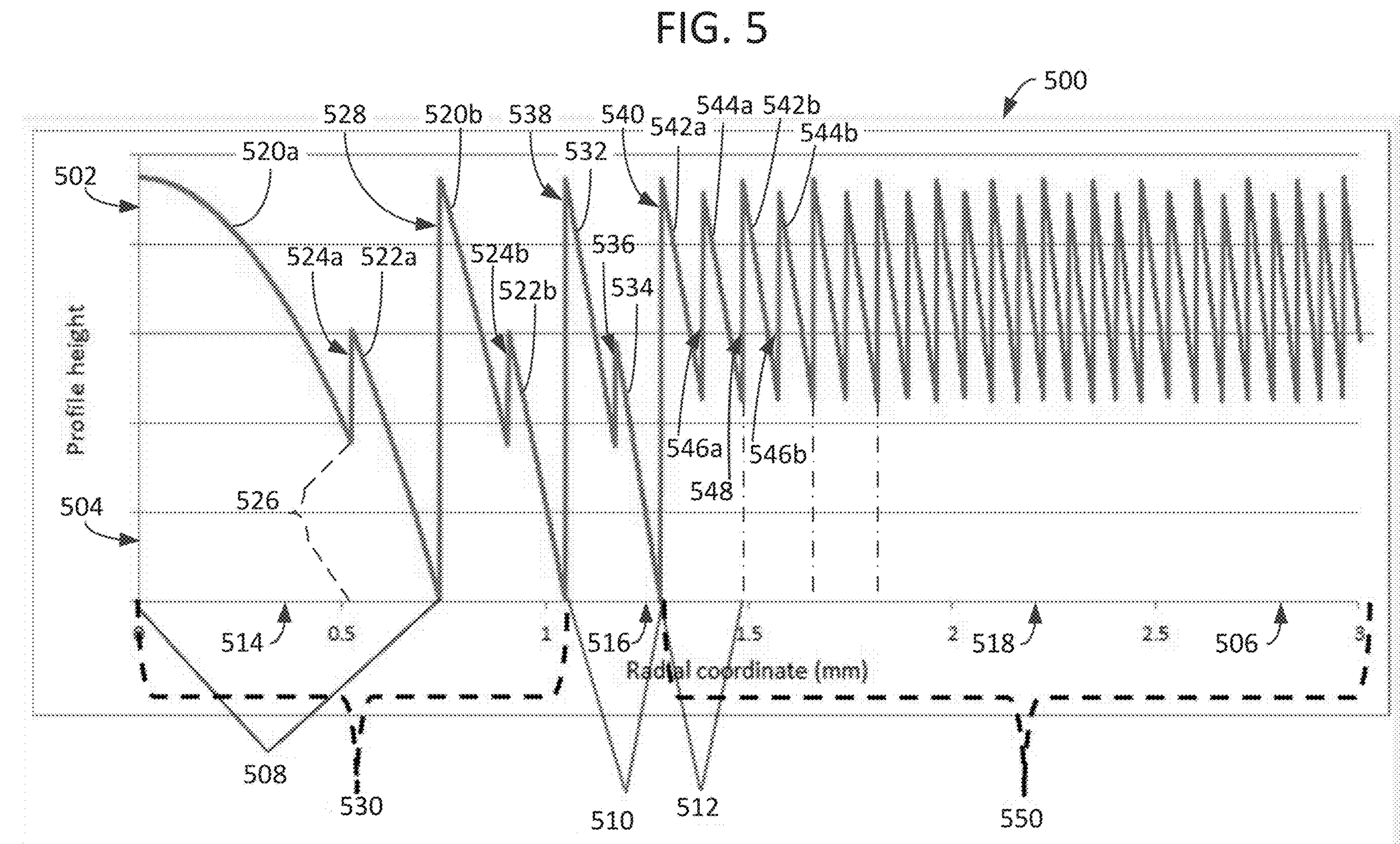
FIG. 5 is a graphical representation illustrating a lens profile for a diffractive lens according to certain embodiments of this disclosure.

FIG. 5 shows a graphical representation illustrating an embodiment of a diffractive profile 500. The diffractive profile 500 may result in a lens having at least two foci, and may include a lens having at least three foci (a trifocal lens). The foci may include a near, a far, and an intermediate focus.

The diffractive profile 500, in the form of a sag profile, is shown extending outward from an optical axis 502. The diffractive zones, or echelettes, are shown extending radially outward from the optical axis 502, and would be arranged around the optical axis 502 (the other half of the diffractive profile 500 is not shown). The diffractive profile 500 is shown relative to the Y axis 504, which represents the height or phase shift of the diffractive profile 500. The height is shown in units of micrometers, and may represent the distance from the base curve of the lens. In other embodiments, other units or scalings may be utilized.

The height or phase shift of the diffractive profile 500 is shown in relation to the radius on the X axis 506 from the optical axis 502. The radius is shown in units of millimeters, although in other embodiments, other units or scalings may be utilized. The diffractive profile 500 may extend outward from the optical axis 502 for a radius of 3.0 millimeters (diameter of 6.0 millimeters), although in other embodiments the diffractive profile 500 may extend for a lesser or greater radius.

The diffractive profile 500 includes three sets 508, 510, 512 of diffractive zones or echelettes. The three sets 508, 510, 512 include a first set 508 positioned at a central zone 514 of the lens. The first set 508 may be repeated once on the central zone 514 (to form two first sets 508 on the central zone). The second set 510 is positioned at a middle zone 516 of the lens. The third set 512 is positioned at a peripheral zone 518 of the lens. The third set 512 may be repeated in series on the peripheral zone 518.

The first set 508 is adjacent the optical axis 502. The first set 508 includes two diffractive zones or echelettes 520*a*, 522*a*. The echelettes 520*a*, 522*a* are connected by a transition zone 524*a* having a step height and a step offset (marked with reference number 526). Each of the echelettes 520*a*, 522*a* of the first set may be configured to have a different profile than each other.

The first set 508 has a profile defined by the shape or slope of the echelettes 520*a*, 522*a*, and the step height and step offsets (as discussed previously) at the transition zone 524*a*, and the height of the first echelette 520*a* at the optical axis 502, and the height of the trailing end of second echelette 522*a* at the transition zone 528. The first echelette 520*a* of the first set 508 has a negative slope extending from its leading end to its trailing edge or end at the transition zone 524*a*. The trailing end has a height corresponding to the step offset at the transition zone 524*a*. The leading end of the second echelette 522*a* is separated from the trailing end of the first echelette 520*a* by the step height corresponding to the transition zone 524*a*.

The second echelette 522*a* extends from its leading end to the trailing end at transition zone 528 and has a negative slope. The slope of the second echelette 522*a* may be different than the slope of the first echelette 520*a*.

The profiles of each of the echelettes 520*a*, 522*a*, are different from each other. The different profiles are due to the differing step heights, step offsets, and slopes of each echelette 520*a*, 522*a*. In r-squared space (discussed previously), the profiles of the echelettes 520*a*, 522*a*, are different from each other, due to the differing step heights, step offsets, and slopes of each echelette 520*a*, 522*a*.

The first set 508 may be disposed twice in series on the central zone 514. The first set 508 may be repeated to form a repeated set 530 on the central zone 514. The other first set may include echelettes 520*b*, 522*b*, and transition zone 524*b*. The first set 508 may connect to the other first set at transition zone 528. The other first set may have the same profile at the first set 508 in r-squared space.

Using the scaling shown in FIG. 5, the repeated first set 530, and the central zone 514, may end at the radial distance of about 1.1 millimeters.

The second set 510 may be adjacent the repeated first set 530. The second set 510 includes two diffractive zones or echelettes 532, 534. The echelettes 532, 534 may be connected by a transition zone 536 having a step height and step offset. The second set 510 may occur once on the middle zone 516 (and the optical surface overall), and thus may not be repeated on the middle zone 516. The second set 510 may connect to the repeated first set 530 via the transition zone 538.

The second set 510 has a profile defined by the shape or slope of the echelettes 532, 534, and the step height and step offsets (as discussed previously) at the transition zones 536, 538, and the height of the trailing end of second echelette 534 at the transition zone 540. The first echelette 532 of the second set 510 has a negative slope extending from its leading end to its trailing edge or end at the transition zone 536. The trailing end has a height corresponding to the step offset at the transition zone 536. The leading end of the second echelette 534 is separated from the trailing end of the first echelette 532 by the step height corresponding to the transition zone 536.

The second echelette 534 extends from its leading end to the trailing end at transition zone 540 and has a negative slope. The slope of the second echelette 534 may be different than the slope of the first echelette 532.

The profiles of each of the echelettes 532, 534, are different from each other. The different profiles are due to the differing step heights, step offsets, and slopes of each echelette 532, 534. In r-squared space (discussed previously), the profiles of the echelettes 532, 534, are different from each other, due to the differing step heights, step offsets, and slopes of each echelette 532, 534.

The profile of the second set 510 is different than the profile of the first set 508. The different profiles are due to the differing step heights, step offsets, and slopes of the echelettes within the respective set 508, 510. In r-squared space, the profile of the second set 510 is different than the profile of the first set 508 due to the differing step heights, step offsets, and slopes of the echelettes within the respective set 508, 510.

Using the scaling shown in FIG. 5, the second set 510, and the central zone 516, may end at the radial distance of about 1.25 millimeters.

The third set 512 may be adjacent the second set 510. The third set 512 includes two diffractive zones or echelettes 542*a*, 544*a*.

The echelettes 542*a*, 544*a* may be connected by a transition zone 546*a* having a step height and step offset. The third set 512 may connect to the second set 510 via the transition zone 540.

The third set 512 has a profile defined by the shape or slope of the echelettes 542*a*, 544*a*, and the step height and step offsets (as discussed previously) at the transition zones 540, 546*a*, and the height of the trailing end of second echelette 544*a* at the transition zone 548. The first echelette 542*a* of the third set 512 has a negative slope extending from its leading end to its trailing edge or end at the transition zone 546*a*. The trailing end has a height corresponding to the step offset at the transition zone 546*a*. The leading end of the second echelette 544*a* is separated from the trailing end of the first echelette 542*a* by the step height corresponding to the transition zone 546*a*.

The second echelette 544*a* extends from its leading end to the trailing end at transition zone 548 and has a negative slope. The slope of the second echelette 544*a* may be different than the slope of the first echelette 542*a*.

The profiles of each of the echelettes 542*a*, 544*a* are different from each other. The different profiles are due to the differing step heights, step offsets, and slopes of each echelette 542*a*, 544*a*. In r-squared space (discussed previously), the profiles of the echelettes 542*a*, 544*a*, are different from each other, due to the differing step heights, step offsets, and slopes of each echelette 542*a*, 544*a*.

The profile of the third set 512 is different than the profile of the first set 508 and the profile of the second set 510. The different profiles are due to the differing step heights, step offsets, and slopes of the echelettes within the respective set 508, 510, 512. In r-squared space, the profile of the third set 512 is different than the profile of the first set 508 and the second set 510 due to the differing step heights, step offsets, and slopes of the echelettes within the respective set 508, 510, 512. Notably, the third set 512 includes step offsets that are greater than either the first set 508 or the second set 510.

The third set 512 may be repeated in series on the peripheral zone 518. The third set 512 may be repeated multiple times in series on the peripheral zone 518. The third set 512 may be repeated to form a repeated set 550 on the peripheral zone 518. An adjacent third set may include echelettes 542*b*, 544*b*, and transition zone 546*b*. The adjacent third set may connect to the third set 512 at transition zone 548. The adjacent third set may have the same profile as the third set 512 in r-squared space. The third sets may be repeated to form twelve sets, as shown in FIG. 5, and in other embodiments may be repeated a greater or lesser number of times.

Using the scaling shown in FIG. 5, the repeated third set 550, and the peripheral zone 518, may end at the radial distance of about 3 millimeters.

The first set 508 repeats in series once. The optical characteristics of the repeated first set may be defined by at least three diffractive orders corresponding to at least three diffractive powers. The repeated first set may produce three diffractive orders that are useful for a patient's vision, corresponding to three diffractive powers that are useful for a patient's vision. The diffractive orders may include a $0^{th}$ order and orders $1^{st}$ through $4^{th}$. The orders $2^{nd}$ through $4^{th}$ may be useful for a patient's vision. The $0^{th}$ and $1^{st}$ orders may be hyperopic (beyond far).

The repeated first set may distribute light to three diffractive orders, with the following light distribution of incident light to each of the three diffractive orders, and the diffractive power shown in Table 1 below:

TABLE 1

| Diffractive order | Diffractive power | Light distribution |
|---|---|---|
| $2^{nd}$ | 4.0D (Far) | 36% |
| $3^{rd}$ | 6.0 D (2 D add) | 23% |
| $4^{th}$ | 8.0D (4 D add) | 26% |

The repeated first set may result in a light distribution with more than 20% of incident light distribution toward a first diffractive power, and more than 20% of incident light distribution towards a second diffractive power. The first diffractive power may be between about 1.75 and 2.25 diopter, and the second diffractive power may be between about 3.75 and 4.25 diopter. The first diffractive power may correspond to a $3^{rd}$ diffractive order and the second diffractive power may correspond to a $4^{th}$ diffractive order.

In one embodiment, the first set 508 may be repeated at least once on the central zone 514.

The second set 510 does not repeat. If the second set 510 were to repeat, then the optical characteristics may be defined by at least three diffractive orders corresponding to at least three diffractive powers. The repeated second set 510 may produce three diffractive orders that are useful for a patient's vision, corresponding to three diffractive powers that are useful for a patient's vision. The diffractive orders may include a $0^{th}$ order and orders $1^{st}$ through $4^{th}$. The orders $2^{nd}$ through $4^{th}$ may be useful for a patient's vision. The $0^{th}$ and $1^{st}$ orders may be hyperopic (beyond far).

If the second set 510 were to repeat, the repeated second set 510 may distribute light to three diffractive orders, with the following light distribution of incident light to each of the three diffractive orders, and the diffractive power shown in Table 2 below:

TABLE 2

| Diffractive order | Diffractive power | Light distribution |
|---|---|---|
| $2^{nd}$ | 4D (Far) | 41% |
| $3^{rd}$ | 6D (2D add) | 15% |
| $4^{th}$ | 8D (4D addd) | 28% |

In one embodiment, the second set 510 may be repeated at least once.

The third set 512 repeats to form a repeated set. The optical characteristics of the repeated third set may be defined by at least three diffractive orders corresponding to at least three diffractive powers. The repeated third set may produce three diffractive orders that are useful for a patient's vision, corresponding to three diffractive powers that are useful for a patient's vision. The diffractive orders may include a $0^{th}$ order and orders $1^{st}$ through $4^{th}$. The orders $2^{nd}$ through $4^{th}$ may be useful for a patient's vision. The $0^{th}$ and $1^{st}$ orders may be hyperopic (beyond far).

The repeated third set may distribute light to three diffractive orders, with the following light distribution of incident light to each of the three diffractive orders, and the diffractive power shown in Table 3 below:

TABLE 3

| Diffractive order | Diffractive power | Light distribution |
|---|---|---|
| $2^{nd}$ | 4D (Far) | 88% |
| $3^{rd}$ | 6D (2D add) | 1% |
| $4^{th}$ | 8D (4D add) | 4% |

The repeated third set may be configured to result in a light distribution with less than 2% of incident light distribution toward a first diffractive power, and less than 5% of incident light distribution toward a second diffractive power. The first diffractive power may be between about 1.75 and 2.25 diopter, and the second diffractive power may be between about 3.75 and 4.25 diopter. The first diffractive power may correspond to a $3^{rd}$ diffractive order, and the second diffractive power may correspond to a $4^{th}$ diffractive order.

In one embodiment, the third set 512 may be repeated at least once on the peripheral zone 518.

The diffractive powers and light distributions listed in each of Tables 1, 2, and 3 may vary to an amount that is "about" the listed amount. In other embodiments, the diffractive orders, powers and light distributions, listed in each of Tables 1, 2, and 3 may be varied as desired.

The add power listed in Tables 1-3 corresponds to 4 diopter of near add power and 2 diopter of intermediate add power. As such, the "Far" power by itself constitutes 4 diopter of diffractive power. This feature may provide improved correction of chromatic aberration for distance.

The diffractive powers of the lens may vary, depending on the desired performance of the design. The diffractive powers as listed in Tables 1-3 are intended for a design that provides adequate visual performance over the entire range of vision from far to intermediate distances and near. Lower diffractive powers may be beneficial if the desired performance is to emphasize good far and intermediate vision, while vision at near distances may be slightly reduced. Such lens design may have a second diffractive add power of 0.58 D, a third diffractive add power of 1.17 D and a fourth diffractive add power of 1.75 D. Some embodiments have diffractive add powers in-between these and those in Tables 1-3.

The combination of the repeating first set 508, non-repeating second set 510, and the repeated third set 512, may result in a diffractive profile producing at least two foci, and at least three foci, for the patient.

In one embodiment, the diffractive profile 500 may be positioned on a surface of a lens that is opposite an aspheric surface. The aspheric surface on the opposite side of the lens may be designed to reduce corneal spherical aberration of the patient.

In one embodiment, one or both optical surfaces may be aspherical, or include a refractive surface designed to extend the depth of focus, or create multifocality.

In one embodiment, a refractive zone on one or both optical surfaces may be utilized that may be the same size or different in size as one of the diffractive zones. The refractive zone includes a refractive surface designed to extend the depth of focus, or create multifocality.

Figure 6:
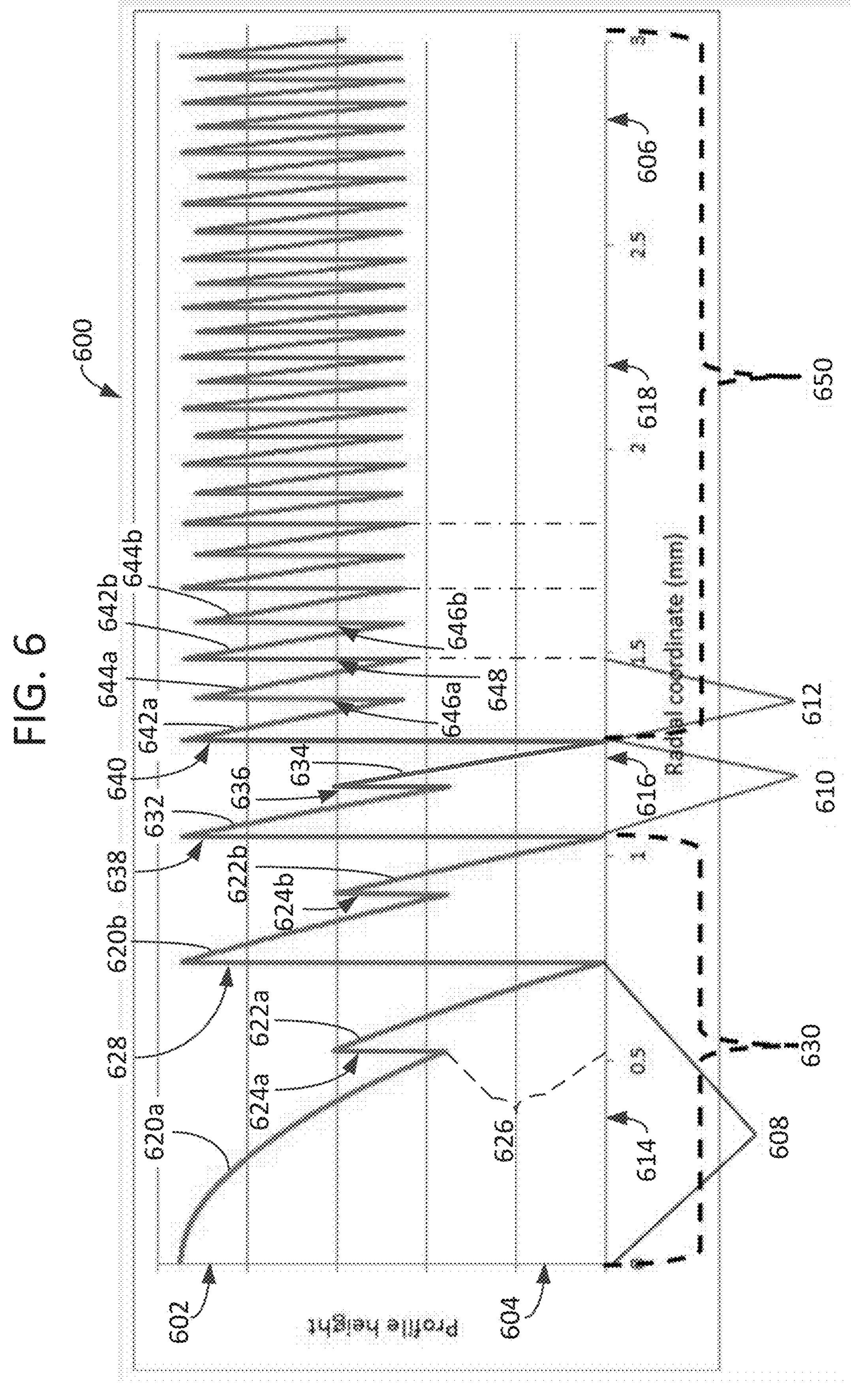
FIG. 6 is a graphical representation illustrating a lens profile for a diffractive lens according to certain embodiments of this disclosure.

FIG. 6 shows a graphical representation illustrating an embodiment of a diffractive profile 600. The diffractive profile 600 may result in a lens having at least two foci, and may include a lens having at least three foci (a trifocal lens). The foci may include a near, a far, and an intermediate focus.

The diffractive profile 600 is configured similarly as the diffractive profile 500 shown in FIG. 5. However, the diffractive profile 600 includes a second set 610 of echelettes in a middle zone 616 that has a profile in r-squared space that is substantially identical to the profile of a first set 608 of echelettes in r-squared space.

Similar to the diffractive profile 500 shown in FIG. 5, the diffractive profile 600 is shown extending outward from an optical axis 602. The diffractive profile 600 is shown relative to the Y axis 604, which represents the height or phase shift of the diffractive profile 600, and is shown in units of micrometers, and may represent the distance from the base curve of the lens.

The height or phase shift of the diffractive profile 600 is shown in relation to the radius on the X axis 606 from the optical axis 602.

The diffractive profile 600 includes three sets 608, 610, 612 of diffractive zones or echelettes. The three sets include a first set 608 positioned at a central zone 614 of the lens. The second set 610 is positioned at a middle zone 616 of the lens. The third set 612 is positioned at a peripheral zone 618 of the lens. The third set 612 may be repeated in series on the peripheral zone 618.

The first set 608 may include two diffractive zones or echelettes 620*a*, 622*a*, which may be connected by transition zone 624*a*. The reference number 626 represents the step offset at the transition zone 624*a*. The profile of the first set 608 may be the same as the profile of the first set 508 shown in FIG. 5. In addition, similar to the first set 508 shown in FIG. 5, the first set 608 may be repeated on the central zone once (to form two first sets 608 on the central zone). The repeated sets may form a repeated first set 630. The properties of the first set 608 and the repeated first set may be the same as the properties of the first set 508 and the repeated first set shown in FIG. 5. The other first set may include echelettes 620*b*, 622*b*, which may be connected by transition zone 624*b*. The other first set may connect to the first set 608 with transition zone 628. The first set 608 may be repeated at least once on the central zone 614.

The second set 610 may include two diffractive zones or echelettes 632, 634, which may be connected by transition zone 636. The second set 610 may be adjacent the repeated first set 608 and may be connected to the repeated first set 608 with a transition zone 638. The profile of the second set 610 in r-squared space is substantially identical to the profile of a first set 608 of echelettes in r-squared space. The step height and offset at transition zone 636 may be substantially identical to the step height and offset at transition zone 624*a*, and the slopes of the echelettes 632, 634 may be substantially identical to those of the echelettes 620*a*, 622*a*. In one embodiment, the second set 610 may not be repeated. In one embodiment, the second set 610 may be repeated at least once.

The third set 612 may include two diffractive zones or echelettes 642*a*, 644*a*, which may be connected by a transition zone 646*a*. The third set 612 may be adjacent the second set 610 and may be connected to the second set 610 with transition zone 640.

The profile of the third set 612 may be same as the profile of the third set 512 shown in FIG. 5. In addition, similar to the third set 512 shown in FIG. 5, the third set 612 may be repeated on the peripheral zone. The repeated sets may form a repeated third set 650. The properties of the third set 612 and the repeated third set may be the same as the properties of the third set 512 and the repeated third set shown in FIG. 5. One such repeated third set may include echelettes 642*b*, 644*b*, which may be connected by transition zone 646*b*. The third set may connect to the other third set 612 with transition zone 648. The third set 612 may be repeated at least once on the peripheral zone 618.

In one embodiment, the second set 610 may be excluded, such that only echelettes on a central zone and echelettes on a peripheral zone may be utilized in a diffractive profile. The echelettes on the central zone may be adjacent the echelettes on the peripheral zone.

In one embodiment, a diffractive profile may be configured such that the second set of echelettes in the middle zone has a profile that is the same as the second set 510 of echelettes shown in FIG. 5, and a first set of echelettes in a central zone has a profile in r-squared space that is substantially identical to the profile in r-squared space as the second set 510 of echelettes shown in FIG. 5.

The diffractive profiles disclosed herein may produce at least two foci, and at least three foci, for the patient.

The embodiments of diffractive profiles disclosed herein may be positioned on a surface of a lens that is opposite an aspheric surface. The aspheric surface on the opposite side of the lens may be designed to reduce corneal spherical aberration of the patient.

The embodiments of diffractive profiles disclosed herein may be utilized with one or both surfaces of the lens that may be aspherical, or include a refractive surface designed to extend the depth of focus, or create multifocality.

The embodiments of diffractive profiles disclosed herein may be utilized with a refractive zone on one or both surfaces of the lens, that may be the same size or different in size as one of the diffractive zones. The refractive zone includes a refractive surface designed to extend the depth of focus, or create multifocality.

Any of the embodiments of lens profiles discussed herein may be apodized to produce a desired result. The apodization may result in the step heights and step offsets of the repeated sets being varied according to the apodization. The sets, however, are still considered to be repeating sets over the optic of the lens.

Systems and Methods for Determining Lens Shape:

FIG. 7 is a simplified block diagram illustrating a system 700 for generating an ophthalmic lens based on a user input.

The system 700 includes a user input module 702 configured to receive user input defining aspects of the user and of a lens. The input may accept an ophthalmic lens prescription for a patient eye. Aspects of a lens may include a multifocal lens prescription, anatomical dimensions like a pupil size performance, and lens dimensions, among other attributes. A multifocal lens prescription can include, for example, a preferred optical power or optical power profile for correcting far vision and an optical power or optical power profile for near vision. In some cases, a multifocal lens prescription can further include an optical power or optical power profile for correcting intermediate vision at two, or in some cases more than two intermediate foci, which may fall between the optical powers or ranges of optical powers described above. A pupil size performance can include a pupil radius of a patient and the visual field to be optimized. These parameters can also be related to patient's life style or profession, so that the design incorporates patient's visual needs as a function of the pupil size. Lens dimensions can include a preferred radius of the total lens, and may further include preferred thickness, or a preferred curvature of one or the other of the anterior surface and posterior surface of the lens.

A multizonal diffractive surface modeling module 704 can receive information about the desired lens from the user input module 702, and can determine aspects of a multizonal lens. For example, the modeling module 704 can determine the shape of one or more echelettes of the diffractive profile of a diffractive multifocal lens, including the positioning, width, step height, and curvature needed to fulfill the multifocal prescription for each subset of the echelettes, as well as the positioning of each subset of echelettes. The multizonal diffractive surface modeling module 704 can further determine the shapes of transition steps between echelettes. For example, transition steps may be smoothed or rounded to help mitigate optical aberrations caused by light passing through an abrupt transition. Such transition zone smoothing, which may be referred to as a low scatter profile, can provide for reductions in dysphotopsia by reducing the errant concentration of incident light behind the lens by the transition zones. By way of further example, echelette ordering, echelette offsets, and echelette boundaries may be adjusted to adjust the step heights between some adjacent echelettes. The generated diffractive profile may be any of the diffractive profiles disclosed in this application.

The multizonal diffractive surface modeling module 704 can be configured to generate performance criteria 712, e.g. via modeling optical properties in a virtual environment. Performance criteria can include the match of the optical power profile of the multizonal lens with the desired optical power profile based on the extended range of vision prescription. The performance criteria can also include the severity of diffractive aberrations caused by lens surface. In some cases, the multizonal surface modeling module 704 can provide a lens surface to a lens fabrication module 708 for facilitating the production of a physical lens, which can be tested via a lens testing module 710 for empirically determining the performance criteria 712, so as to identify optical aberrations and imperfections not readily discerned via virtual modeling, and to permit iteration. The lens fabrication module may comprise a manufacturing assembly that may fabricate the ophthalmic lens based on the diffractive profile.

A refractive surface modeling module 706 can receive information from the user input 702 and multizonal surface modeling modules 704 in order to determine refractive aspects of the lens. For example, provided with a multifocal prescription and a set of add powers that can be generated by a diffractive profile, the refractive surface modeling module 706 can provide a refractive geometry configured to provide a base power which, when combined with the diffractive surface, meets the requirements of the multifocal lens prescription. The refractive surface modeling module 706 can also generate performance criteria 712, and can contribute to providing a lens surface to a lens fabrication module 708 for facilitating the production of the physical lens.

FIG. 8 is an example process 800 for generating a diffractive lens surface, in accordance with embodiments. The process 800 may be implemented in conjunction with, for example, the system 700 shown in FIG. 7. Some or all of the process 800 (or any other processes described herein, or variations, and/or combinations thereof) may be performed under the control of one or more computer systems configured with executable instructions and may be implemented as code (e.g., executable instructions, one or more computer programs, or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

The process 800 may include a method of designing an intraocular lens and may include receiving an input of an ophthalmic lens prescription, which may be a multifocal lens prescription (act 802). The input can include, e.g., a desired optical power profile for correcting impaired distance vision, a desired optical power profile for correcting impaired intermediate distance vision, a desired optical power profile for accommodating near vision, and any suitable combination of the above. Based on a desired optical power profile, a diffractive profile can be defined and generated including a central zone, a peripheral zone, and a middle zone positioned between the central zone and the peripheral zone. The generated diffractive profile may include a central zone including a first set of two echelettes arranged around the optical axis, the first set having a profile in r-squared space, the first set being repeated once in series on the central zone (act 804). The generated diffractive profile may include a middle zone including a second set of two echelettes arranged around the optical axis, the second set having a profile in r-squared space that is different than the profile of the first set (act 806). The generated diffractive profile may include a peripheral zone including a third set of two echelettes arranged around the optical axis, the third set having a profile in r-squared space that is different than the profile of the first set and the profile of the second set, the third set being repeated in series on the peripheral zone (act 808).

In one embodiment, the diffractive profile may be generated and utilized that includes a central zone and a peripheral zone. The central zone may include a first set of two echelettes arranged around an optical axis, the first set having a profile in r-squared space, the first set being repeated in series at least once on the central zone. The peripheral zone may include a second set of two echelettes arranged around the optical axis, the second set having a profile in r-squared space that is different than the profile of the first set, the second set being repeated in series at least once on the peripheral zone.

In one embodiment, the diffractive profile may include a middle zone positioned between the central zone and the peripheral zone. The middle zone may include a third set of two echelettes arranged around the optical axis, the third set having a profile in r-squared space that is substantially identical to the profile of the first set (in the central zone).

The diffractive lens profile of the multizonal diffractive lens surface may be used in combination with a known refractive base power. To that end, a refractive lens surface may be generated having a base power that, in combination with the diffractive lens surface, meets the multifocal lens prescription (act 810). A total lens surface can be generated based on both the refractive lens surface and the diffractive lens surface (act 812). The refractive lens surface can include a refractive lens curvature on the anterior surface of the lens, the posterior surface of the lens, or both. Instructions can be generated to fabricate an intraocular lens based on the generated total lens surface (act 814). A manufacturing assembly may fabricate the ophthalmic lens based on the instructions. The methods herein are not limited to the examples of diffractive profiles discussed here, and may extend to any of the diffractive lens profiles and ophthalmic lenses disclosed in this application.

Figure 9:
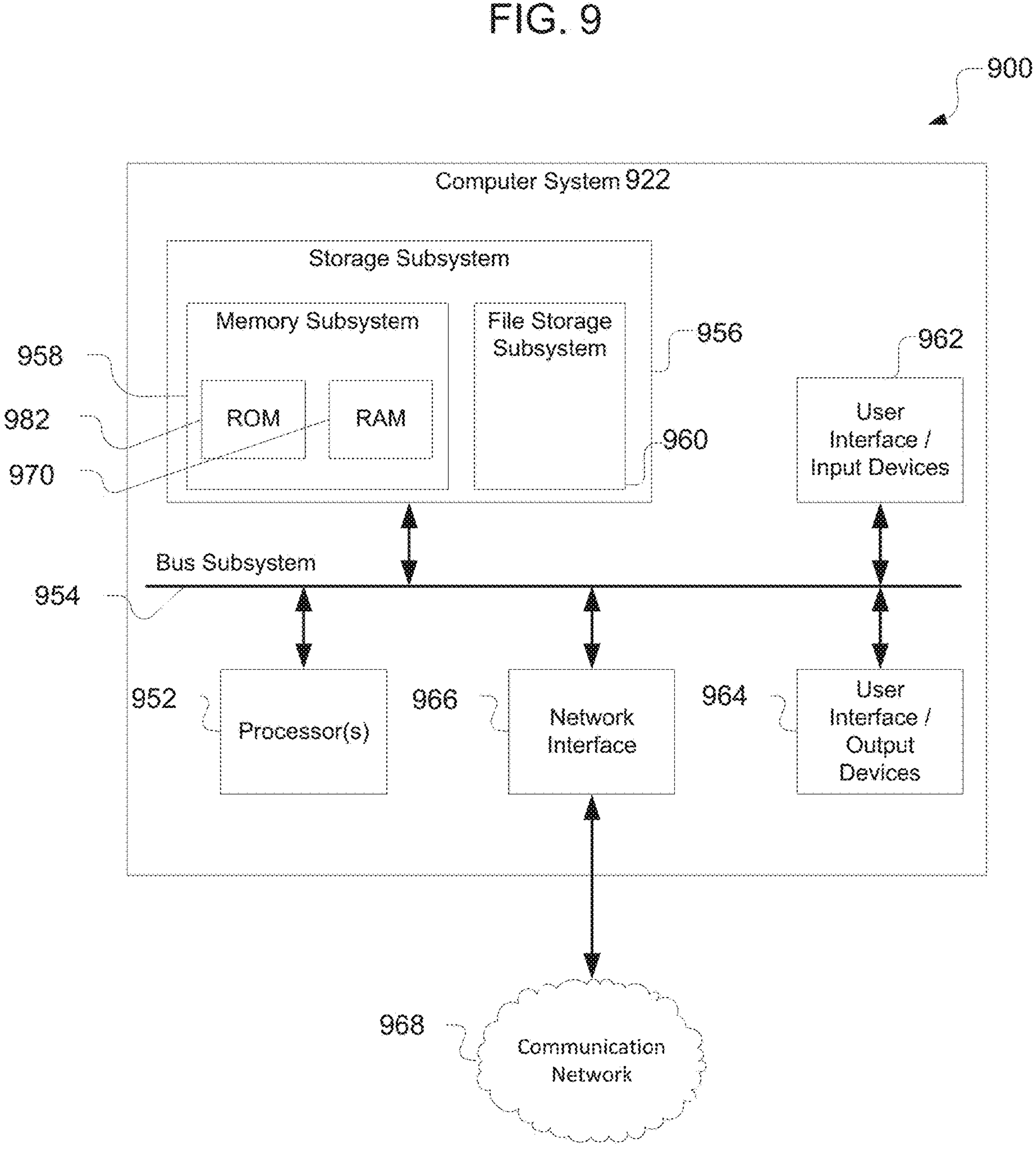
FIG. 9 illustrates an example computing environment for facilitating the systems and processes of FIGS. 7 and 8.

Computational Methods:

FIG. 9 is a simplified block diagram of an exemplary computing environment 900 that may be used by systems for generating the diffractive profiles and ophthalmic lenses of the present disclosure. Computer system 922 typically includes at least one processor 952 which may communicate with a number of peripheral devices via a bus subsystem 954. These peripheral devices may include a storage subsystem 956 comprising a memory subsystem 958 and a file storage subsystem 960, user interface input devices 962, user interface output devices 964, and a network interface subsystem 966. Network interface subsystem 966 provides an interface to outside networks 968 and/or other devices, such as the lens fabrication module 708 or lens testing module 710 of FIG. 7.

User interface input devices 962 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 962 will often be used to download a computer executable code from a tangible storage media embodying any of the methods of the present disclosure. In general, use of the term “input device” is intended to include a variety of conventional and proprietary devices and ways to input information into computer system 922.

User interface output devices 964 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term “output device” is intended to include a variety of conventional and proprietary devices and ways to output information from computer system 922 to a user.

Storage subsystem 956 can store the basic programming and data constructs that provide the functionality of the various embodiments of the present disclosure. For example, a database and modules implementing the functionality of the methods of the present disclosure, as described herein, may be stored in storage subsystem 956. These software modules are generally executed by processor 952. In a distributed environment, the software modules may be stored on a plurality of computer systems and executed by processors of the plurality of computer systems. Storage subsystem 956 typically comprises memory subsystem 958 and file storage subsystem 960. Memory subsystem 958 typically includes a number of memories including a main random access memory (RAM) 970 for storage of instructions and data during program execution and/or a read only member (ROM) 982.

Various computational methods discussed above, e.g. with respect to generating a multizonal lens surface, may be performed in conjunction with or using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

What is claimed is:

1. A method of designing an intraocular lens, the method comprising:

defining a diffractive profile including:

a central zone, a peripheral zone, and a middle zone positioned between the central zone and the peripheral zone, the central zone includes a first set of two echelettes arranged around an optical axis, the first set having a profile in r-squared space, the first set being disposed twice in series on the central zone to form a repeated first set, the middle zone includes a second set of two echelettes arranged around the optical axis, the second set being adjacent the repeated first set, the second set having a profile in r-squared space that is different than the profile of the first set, the second set occurring once on the middle zone and not being repeated on the middle zone, and the peripheral zone includes a third set of two echelettes arranged around the optical axis, the third set being adjacent the second set, the third set having a profile in r-squared space that is different than the profile of the first set and the profile of the second set, the third set being repeated in series at least once on the peripheral zone to form a repeated third set, wherein, for each of the first set, the second set, and the third set, the two echelettes are connected by a transition zone having a step height and a step offset from a base curve; and generating a diffractive lens surface based on the diffractive profile.

2. The method of claim 1, wherein each of the two echelettes of the first set have a different profile than each other in r-squared space, and each of the two echelettes of the second set have a different profile than each other in r-squared space, and each of the two echelettes of the third set have a different profile than each other in r-squared space.

* * * * *